(12) United States Patent
Link et al.

(10) Patent No.: US 8,748,649 B2
(45) Date of Patent: *Jun. 10, 2014

(54) DI-FLUORO CONTAINING COMPOUNDS AS CYSTEINE PROTEASE INHIBITORS

(71) Applicant: ViroBay, Inc., Menlo Park, CA (US)

(72) Inventors: John O. Link, San Francisco, CA (US); Craig J. Mossman, Saratoga, CA (US); Jie Liu, Shanghai (CN); Soon Hyung Woo, Palo Alto, CA (US)

(73) Assignee: Virobay, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/719,024

(22) Filed: Dec. 18, 2012

(65) Prior Publication Data

US 2014/0018421 A1 Jan. 16, 2014

Related U.S. Application Data

(63) Continuation of application No. 13/004,834, filed on Jan. 11, 2011, now Pat. No. 8,367,732, which is a continuation of application No. 12/060,774, filed on Apr. 1, 2008, now Pat. No. 7,893,112, which is a continuation-in-part of application No. 11/866,836, filed on Oct. 3, 2007, now Pat. No. 7,781,487.

(60) Provisional application No. 60/849,587, filed on Oct. 4, 2006.

(51) Int. Cl.
C07C 255/46 (2006.01)
A61K 31/26 (2006.01)

(52) U.S. Cl.
CPC ............... *C07C 255/46* (2013.01); *A62K 31/26* (2013.01)
USPC .......................................... 558/426; 514/521

(58) Field of Classification Search
CPC ........................................................ C07C 255/46
USPC .......................................... 558/426; 514/521
See application file for complete search history.

(56) References Cited

U.S. PATENT DOCUMENTS

| | | | |
|---|---|---|---|
| 6,420,364 B1 | 7/2002 | Emmanuel et al. | |
| 6,506,733 B1 | 1/2003 | Buysse et al. | |
| 6,730,671 B2 | 5/2004 | Cywin et al. | |
| 7,312,211 B2 | 12/2007 | Bekkali et al. | |
| 7,781,487 B2 * | 8/2010 | Link et al. | 514/646 |
| 7,893,112 B2 * | 2/2011 | Link et al. | 514/620 |
| 8,367,732 B2 * | 2/2013 | Link et al. | 514/620 |
| 2003/0092634 A1 | 5/2003 | Buysse et al. | |
| 2003/0232863 A1 | 12/2003 | Bayly et al. | |
| 2004/0127426 A1 | 7/2004 | Graupe et al. | |
| 2005/0014941 A1 | 1/2005 | Black et al. | |
| 2005/0182096 A1 | 8/2005 | Link et al. | |
| 2005/0240023 A1 | 10/2005 | Bayly et al. | |
| 2006/0111440 A1 | 5/2006 | Gauthier et al. | |

FOREIGN PATENT DOCUMENTS

| | | |
|---|---|---|
| CN | 1638757 A | 7/2005 |
| CN | 1842515 A | 10/2006 |
| CN | 1898218 A | 1/2007 |
| EP | 0623627 A1 | 11/1994 |
| JP | 2005-526753 A | 9/2005 |
| JP | 2007-503401 A | 2/2007 |
| JP | 2010-505872 A | 2/2010 |
| WO | WO 99/24460 A3 | 5/1999 |
| WO | WO 00/51998 | 9/2000 |
| WO | WO 00/55125 A2 | 9/2000 |
| WO | WO 00/55144 A1 | 9/2000 |
| WO | WO 01/19796 A1 | 3/2001 |
| WO | WO 01/19816 A1 | 3/2001 |
| WO | WO 01/49288 A1 | 7/2001 |
| WO | WO 01/68645 A2 | 9/2001 |
| WO | WO 02/20485 A1 | 3/2002 |
| WO | WO 02/069901 A2 | 9/2002 |
| WO | WO 02/098850 A2 | 12/2002 |
| WO | WO 03/024924 A1 | 3/2003 |
| WO | WO 03/029200 A2 | 4/2003 |
| WO | WO 03/075836 A2 | 9/2003 |
| WO | WO 03/097617 A1 | 11/2003 |
| WO | WO 2004/083182 A1 | 3/2004 |
| WO | WO 2004/033445 A1 | 4/2004 |
| WO | WO 2004/108661 A1 | 12/2004 |
| WO | WO 2005/002454 A1 | 3/2005 |
| WO | WO 2005/021487 A1 | 3/2005 |
| WO | WO 2005/028429 A2 | 3/2005 |
| WO | WO 2005/040142 A1 | 5/2005 |
| WO | WO 2005/058348 A1 | 6/2005 |
| WO | WO 2005/063742 A2 | 7/2005 |
| WO | WO 2005/074904 A2 | 8/2005 |
| WO | WO 2006/034004 A2 | 3/2006 |
| WO | WO 2008/042968 A2 | 4/2008 |

OTHER PUBLICATIONS

Bundgaard, et al. "A Novel Solution-Stable, Water-Soluble Prodrug Type for Drugs Containing a Hydroxyl or an NH-Acidic Group," J. Med. Chem., 1998, vol. 32, No. 12, pp. 2503-2507.

Gong, Y. et al. "Convenient Substitution of Hydroxypyridines with Trifluoroacetaldehyde Ethyl Hemiacetal," Journal of Heterocyclic Chemistry 2001, vol. 38, No. 1, pp. 25-28.

Greenspan, et al. "Identification of Dipeptidyl Nitriles as Potent and Selective Inhibitors of Cathepsin B through Structure-Based Drug Design," J. Med. Chem., 2001, vol. 44, pp. 4524-4534.

Volonterio, et al. "Solution/solid-phase synthesis of partially modified retro-ϕ [NHCH(CF$_3$)]—peptidyl hydroxamates," Tetrahedron Letters, 2001, vol. 42, pp. 3141-3144.

\* cited by examiner

*Primary Examiner* — Yong Chu
(74) *Attorney, Agent, or Firm* — Kilpatrick Townsend & Stockton LLP

(57) ABSTRACT

The present invention is directed to compounds that are inhibitors of cysteine proteases, in particular, cathepsins B, K, L, F, and S, and are therefore useful in treating diseases mediated by these proteases. The present invention is directed to pharmaceutical compositions comprising these compounds and processes for preparing them.

1 Claim, No Drawings

DI-FLUORO CONTAINING COMPOUNDS AS CYSTEINE PROTEASE INHIBITORS

CROSS-REFERENCES TO RELATED APPLICATIONS

This application is a Continuation of U.S. Ser. No. 13/004,838, filed Jan. 11, 2011, now U.S. Pat. No. 8,367,732, which is a Continuation of U.S. Ser. No. 12/060,774, filed Apr. 1, 2008, now U.S. Pat. No. 7,893,112, which is a Continuation in Part of U.S. Ser. No. 11/866,836, filed Oct. 3, 2007, now issued as U.S. Pat. No. 7,781,487, which claims the benefit of Provisional Application Ser. No. 60/849,587, filed Oct. 4, 2006, each of which is incorporated herein by reference in its entirety.

BACKGROUND OF THE INVENTION

The present invention is directed to compounds that are inhibitors of cysteine proteases, in particular, cathepsins B, K, L, F, and S and are therefore useful in treating diseases mediated by these proteases. The present invention is also directed to pharmaceutical compositions comprising these compounds and processes for preparing them.

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increased expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteoarthritis, *pneumocystis carinii*, acute pancreatitis, inflammatory airway disease and bone and joint disorders.

The prominent expression of cathepsin K in osteoclasts and osteoclast-related multinucleated cells and its high collagenolytic activity suggest that the enzyme is involved in ososteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as several disease states, including, but not limited to, metastasis of melanomas.

Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis, neuropathic pain, and Hashimoto's thyroiditis. In addition, cathepsin S is implicated in: allergic disorders, including, but not limited to asthma; and allogeneic immune responses, including, but not limited to, rejection of organ transplants or tissue grafts.

In view of the number of diseases wherein it is recognized that an increase in cysteine protease activity contributes to the pathology and/or symptomatology of the disease, molecules which inhibit the activity of this class of enzymes, in particular molecules which inhibitor cathepsins B, K, L, F, and/or S, will therefore be useful as therapeutic agents.

BRIEF SUMMARY OF THE INVENTION

In one aspect, this invention is directed to a compound of Formula (I):

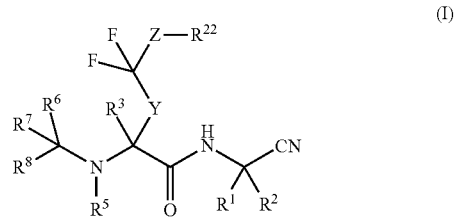

wherein:
  $R^1$ is hydrogen, alkyl, haloalkyl, or alkoxyalkyl;
  $R^2$ is hydrogen, alkyl, haloalkyl, carboxyalkyl, alkoxycarbonylalkyl, cycloalkyl, cycloalkylalkyl, aryl, aralkyl, heteroaryl, heteroaralkyl, heterocyclyl, heterocyclylalkyl, cyano, or -alkylene-X—$R^9$ (where X is —O—, —$NR^{10}$—, —$CONR^{11}$—, —$S(O)_{n1}$—, —$NR^{12}CO$—, —CO—, or —C(O)O—, where n1 is 0-2 and $R^9$, $R^{10}$, $R^{11}$, and $R^{12}$ are independently hydrogen, alkyl, haloalkyl, cycloalkyl, cycloalkylalkyl, aryl, aralkyl, heteroaryl, or heteroaralkyl); wherein the aromatic or alicyclic ring in $R^2$ is optionally substituted with one, two, or three $R^a$ independently selected from alkyl, haloalkyl, alkoxy, hydroxy, haloalkoxy, halo, carboxy, alkoxycarbonyl, amino, monsubstituted amino, disubstituted amino, nitro, aryloxy, benzyloxy, acyl, or arylsulfonyl, and further wherein the aromatic or alicyclic ring in $R^a$ is optionally substituted with one or two substituents independently selected from alkyl, halo, alkoxy, haloalkyl, haloalkoxy, hydroxy, amino, alkylamino, dialkylamino, carboxy, or alkoxycarbonyl; or
  $R^1$ and $R^2$ taken together with the carbon atom to which both $R^1$ and $R^2$ are attached form
    (i) cycloalkylene optionally substituted with one or two $R^b$ independently selected from alkyl, halo, alkylamino, dialkylamino, aryl, aralkyl, cycloalkyl, cycloalkylalkyl, heteroaryl, heteroaralkyl, alkoxycarbonyl, or aryloxycarbonyl;
    (ii) a four-atom heterocyclylalkylene ring; or
    (iii) heterocyclylalkylene optionally substituted with one to four $R^c$ independently selected from alkyl, haloalkyl, hydroxy, hydroxyalkyl, alkoxyalkyl, alkoxyalkyloxyalkyl, aryboxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —$S(O)_{n2}R^{14}$, -alkylene-$S(O)_{n2}$—$R^{15}$, —$COOR^{16}$, -alkylene-$COOR^{17}$, —$CONR^{18}R^{19}$, or -alkylene-$CONR^{20}R^{21}$ (where n2 is 0-2 and $R^{14}$-$R^{18}$ and $R^{20}$ are independently hydrogen, alkyl, haloalkyl, aryl, aralkyl, heteroaryl, heteroaralkyl, cycloalkyl, cycloalkylalkyl, or heterocyclyl and $R^{19}$ and $R^{21}$ are independently hydrogen or alkyl);
  wherein the aromatic or alicyclic ring in the groups attached to cycloalkylene or heterocyclylalkylene is optionally substituted with one, two, or three substituents independently selected from alkyl, haloalkyl, cycloalkyl, cycloalkylalkyl, aralkyl, aryloxycarbonyl, alkoxy, hydroxy, haloalkoxy, halo, carboxy, alkoxycarbonyl, amino, monsubstituted amino, disubstituted amino, or acyl;

R³ is hydrogen or alkyl;

R⁵ is hydrogen or alkyl;

R⁶ is hydrogen, alkyl, haloalkyl, cycloalkyl, aryl, aralkyl, heteroaryl, heteroaralkyl, heterocyclyl, or -alkylene-X²—R²⁵ (where X² is —NR²⁶—, —O—, —S(O)$_{n4}$—, —CO—, —COO—, —COO—, —NR²⁶CO—, —CONR²⁶—, —NR²⁶SO₂—, —SO₂NR²⁶—, —NR²⁶COO—, —OCONR²⁶—NR²⁶CONR²⁷—, or —NR²⁶SO₂NR²⁷—, where R²⁶ and R²⁷ are independently hydrogen, alkyl, or acyl, n4 is 0-2, and R²⁵ is hydrogen, alkyl, haloalkyl, cycloalkyl, cycloalkylalkyl, heterocyclyl, heterocyclylalkyl, aryl, aralkyl, heteroaryl, or heteroaralkyl), wherein said alkylene chain in R⁶ is optionally substituted with one to six halo and the aromatic or alicyclic rings in R⁶ are optionally substituted by one, two, or three R$^e$ independently selected from alkyl, halo, hydroxy, hydroxyalkyl, hydroxyalkoxy, alkoxy, alkoxyalkyl, alkoxyalkyloxy, haloalkyl, haloalkoxy, oxo, cyano, nitro, acyl, aryl, aralkyl, aryloxy, aralkyloxy, arylsulfonyl, heteroaryl, heteroaralkyl, heteroaryloxy, heteroaralkyloxy, heteroarylsulfonyl, heterocyclyl, heterocyclylalkyl, cycloalkyl, cycloalkylalkyl, carboxy, alkoxycarbonyl, alkylsulfonyl, aminosulfonyl, or aminoalkyl, and further where the aromatic or alicyclic ring in R$^e$ is optionally substituted with one, two or three R$^f$ independently selected from alkyl, alkoxy, haloalkyl, haloalkoxy, halo, hydroxy, carboxy, cyano, nitro, aryl or cycloalkyl;

R⁷ is haloalkyl or haloalkoxy, either of which is optionally substituted with alkoxy or alkoxyalkyloxy;

R⁸ is hydrogen, alkyl, alkoxyalkyl or haloalkyl; or

R⁶ and R⁸ together with the carbon atom to which they are attached form cycloalkylene or heterocyclylalkylene wherein said cycloalkylene is optionally substituted with one to four substituents independently selected from alkyl, halo, haloalkyl, hydroxy, or alkoxy and heterocyclylalkylene is optionally substituted with one or two substituents independently selected from alkyl, halo, haloalkyl, cycloalkyl, hydroxy, or alkoxy;

R²² is hydrogen, fluoro, alkyl, haloalkyl, cycloalkyl, cycloalkylalkyl, heterocyclyl, aryl, aralkyl, heteroaryl, heteroaralkyl, heterocyclyl, or heterocyclylalkyl, wherein the aromatic or alicyclic ring in R²² is optionally substituted with one, two, or three R$^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monosubstituted amino, disubstituted amino, or acyl;

Y is -alkylene- or -alkylene-O—, wherein the alkylene group is optionally substituted with one to six fluoro atoms; and Z is a direct bond, —O—, -alkylene- or —O-alkylene, wherein the alkylene portion is optionally substituted with one to six fluoro atoms;

or, a pharmaceutically acceptable salt thereof.

In a second aspect, this invention is directed to a pharmaceutical composition comprising a compound of Formula (I), individual stereoisomers or a mixture thereof; or a pharmaceutically acceptable salt thereof in admixture with one or more suitable excipients.

In a third aspect, this invention is directed to a method for treating a disease in an animal mediated by cysteine proteases, the cysteine protease being cathepsin S in one embodiment, which method comprises administering to the animal a pharmaceutical composition comprising a therapeutically effective amount of a compound of Formula (I), an individual stereoisomer or a mixture thereof or a pharmaceutically acceptable salt thereof in admixture with one or more suitable excipients.

In a fourth aspect, this invention is directed to processes for preparing compounds of Formula (I) and the pharmaceutically acceptable salts thereof.

In a fifth aspect, this invention is directed to a method of treating a patient undergoing a therapy wherein the therapy causes an immune response, in one embodiment a deleterious immune response, in the patient comprising administering to the patient a compound of Formula (I), an individual stereoisomer or a mixture thereof; or a pharmaceutically acceptable salt thereof. In one embodiment, the immune response is mediated by MHC class II molecules. The compound of this invention can be administered prior to, simultaneously, or after the therapy. In one embodiment, the therapy involves treatment with a biologic. In another embodiment, the therapy involves treatment with a small molecule.

The biologic can be a protein or an antibody. In one embodiment, the biologic is a monoclonal antibody. The biologic can be, but is not limited to, Remicade®, Refacto®, Referon-A®, Factor VIII, Factor VII, Betaserono®, Epogeno®, Enbrel®, Interferon beta, Botox®, Fabrazyme®, Elspar®, Cerezyme®, Myobloc®, Aldurazyme®, Verluma®, Interferon alpha, Humira®, Aranesp®, Zevalin® or OKT3. In one embodiment, the treatment involves use of heparin, low molecular weight heparin, procainamide or hydralazine.

In a sixth aspect, this invention is directed to a method of treating immune response in an animal that is caused by administration of a biologic to the animal, which method comprises administering to the animal in need of such treatment a therapeutically effective amount of a compound of Formula (I), an individual stereoisomer or a mixture thereof, or a pharmaceutically acceptable salt thereof.

In a seventh aspect, this invention is directed to a method of conducting a clinical trial for a biologic comprising administering to an individual participating in the clinical trial a compound of Formula (I), an individual stereoisomer or a mixture thereof or a pharmaceutically acceptable salt thereof with the biologic.

In an eighth aspect, this invention is directed to a method of prophylactically treating a person undergoing treatment with a biologic with a compound of Formula (I), an individual stereoisomer or a mixture thereof or a pharmaceutically acceptable salt thereof to treat the immune response caused by the biologic in the person.

In a ninth aspect, this invention is directed to a method of determining the loss in the efficacy of a biologic in an animal due to the immune response caused by the biologic, the method comprising administering the biologic to the animal in the presence and absence of a compound of Formula (I); an individual stereoisomer or a mixture thereof or a pharmaceutically acceptable salt thereof.

In a tenth aspect, this invention is directed to a method of improving efficacy of a biologic in an animal comprising administering the biologic to the animal with a compound of Formula (I), an individual stereoisomer or a mixture thereof or a pharmaceutically acceptable salt thereof.

In an eleventh aspect, this invention is directed to the use of a compound of Formula (I), an individual stereoisomer or a mixture thereof or a pharmaceutically acceptable salt thereof for the manufacture of a medicament. In one embodiment, the medicament is for use in the treatment of a disease mediated by cysteine proteases, such as for example Cathepsin S.

In a twelfth aspect, this invention is directed to the use of a compound of Formula (I), an individual stereoisomer or a mixture thereof or a pharmaceutically acceptable salt thereof for the manufacture of a medicament for combination therapy with a biologic, wherein the compound of this invention treats the immune response caused by the biologic. In one embodiment, the compound(s) of the invention is administered prior to the administration of the biological agent. In another embodiment, the compound(s) of the invention is administered concomitantly with the biological agent. In a further embodiment, the compound(s) of the invention is administered after the administration of the biological agent.

BRIEF DESCRIPTION OF THE DRAWINGS

Not applicable

DETAILED DESCRIPTION OF THE INVENTION

Throughout this specification and the claims that follow, unless the context requires otherwise, the word "comprise" and variations such as "comprises" and "comprising" will be understood to imply the inclusion of a stated integer or step or group of integers or steps but not the exclusion of any other integer or step or group of integers or steps.

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Furthermore, as used in the specification and appended claims, unless specified to the contrary, the following terms have the meaning indicated:

"Alicyclic" means a moiety characterized by arrangement of the carbon atoms in closed non-aromatic ring structures e.g., cycloalkyl and heterocyclyl rings as defined herein.

"Alkyl" represented by itself means a straight or branched, saturated aliphatic radical containing one to six carbon atoms, unless otherwise indicated e.g., alkyl includes methyl, ethyl, propyl, isopropyl, butyl, sec-butyl, isobutyl, tert-butyl, and the like.

"Alkylene", unless indicated otherwise, means a straight or branched, saturated aliphatic, divalent radical having the number of one to six carbon atoms, e.g., methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—) 2-methyltetramethylene (—CH$_2$CH(CH$_3$)CH$_2$CH$_2$—), pentamethylene (—CH$_2$CH$_2$CH$_2$CH$_2$CH$_2$—), and the like.

"Amino" means the —NH$_2$ radical. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Alkylamino" or "dialkylamino" refers to a —NHR or a —NRR' radical, respectively, where R and R' are independently an alkyl group as defined above, e.g., methylamino, dimethylamino, and the like.

"Alkoxy" refers to a —OR radical where R is an alkyl group as defined above, e.g., methoxy, ethoxy, and the like.

"Alkoxycarbonyl" refers to a —C(O)OR radical where R is an alkyl group as defined above, e.g., methoxycarbonyl, ethoxycarbonyl, and the like.

"Alkoxycarbonylalkyl" means an -(alkylene)-C(O)OR radical where R is alkyl as defined above, e.g., methoxycarbonylmethyl, 2-, or 3-ethoxycarbonylmethyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxyalkyloxy" refers to a —OR radical where R is alkoxyalkyl as defined above, e.g., methoxymethyloxy, methoxyethyloxy, and the like.

"Alkoxyalkyloxyalkyl" refers to an -(alkylene)-O-(alkylene)-OR radical where R is an alkyl group as defined above, e.g., 2-methoxyethyloxymethyl, 3-methoxypropyloxyethyl, and the like.

"Aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, or —COR$^a$ where R$^a$ is alkyl, and R' is hydrogen or alkyl as defined above, e.g., aminomethyl, methylaminoethyl, dimethylaminoethyl, 1,3-diaminopropyl, acetylaminopropyl, and the like e.g., aminosulfonyl, methylaminosulfonyl, dimethylaminosulfonyl, and the like.

"Aminosulfonyl" refers to a —SO$_2$R radical where R is —NRR' where R is hydrogen, alkyl, or —COR$^a$ where R$^a$ is alkyl, and R' is hydrogen or alkyl as defined above, e.g., aminosulfonyl, methylaminosulfonyl, dimethylaminosulfonyl, and the like.

"Alkylsulfonyl" refers to a —SO$_2$R radical where R is an alkyl group as defined above, e.g., methylsulfonyl, ethylsulfonyl, and the like.

"Acyl" refers to a —COR radical where R is hydrogen, alkyl, haloalkyl, aryl, aralkyl, heteroaryl, heteroaralkyl, or heterocyclyl as defined herein, e.g., formyl, acetyl, trifluoroacetyl, benzoyl, piperazin-1-ylcarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" refers to a moiety wherein the constituent atoms make up an unsaturated ring system, all atoms in the ring system are sp$^2$ hybridized and the total number of pi electrons is equal to 4n+2, "Aryl" refers to a monocyclic or fused bicyclic ring assembly containing 6 to 10 ring carbon atoms wherein each ring is aromatic, e.g., phenyl, naphthyl, and the like.

"Aralkyl" refers to an -(alkylene)-R radical where R is aryl as defined above, e.g., benzyl, phenethyl, and the like.

"Aryloxy" refers to a —OR radical where R is aryl as defined above, e.g., phenoxy and the like.

"Aralkyloxy" refers to a —OR radical where R is aralkyl as defined above, e.g., benzyloxy and the like.

"Aryloxyalkyl" refers to an -(alkylene)-OR radical where R is aryl as defined above, e.g., phenoxymethyl, 2- or 3-phenoxymethyl, and the like "Aryloxycarbonyl" refers to a —C(O)OR radical where R is aryl as defined above, e.g., phenyloxycarbonyl and the like.

"Arylsulfonyl" refers to a —SO$_2$R radical where R is an aryl group as defined above, e.g., phenylsulfonyl and the like.

"Biologic" means a therapeutic agent originally derived from living organisms for the treatment or management of a disease. Examples include, but are not limited to, proteins (recombinant and plasma derived), monoclonal or polyclonal antibodies, humanized or murine antibodies, toxins, hormones, and the like. Biologics are currently available for the treatment of a variety of diseases such as cancer, rheumatoid arthritis, and haemophilia.

"Carboxy" refers to the —C(O)OH radical.

"Carboxyalkyl" refers to an -(alkylene)-C(O)OH radical, e.g., carboxymethyl, carboxyethyl, and the like.

"Cycloalkyl" refers to a monovalent saturated or partially unsaturated, monocyclic ring containing three to eight ring carbon atoms, e.g., cyclopropyl, cyclobutyl, cyclopentyl, cyclohexyl, cyclohexenyl, 2,5-cyclohexadienyl, and the like.

"Cycloalkylalkyl" refers to an -(alkylene)-R radical where R is cycloalkyl as defined above, e.g., cyclopropylmethyl, cyclobutylethyl, cyclobutylmethyl, and the like "Cycloalkylene" refers to a divalent saturated or partially unsaturated monocyclic ring containing three to eight ring carbon atoms. For example, the instance wherein "R$^1$ and R$^2$ together with the carbon atom to which both R$^1$ and R$^2$ are attached form cycloalkylene" includes, but is not limited to, the following:

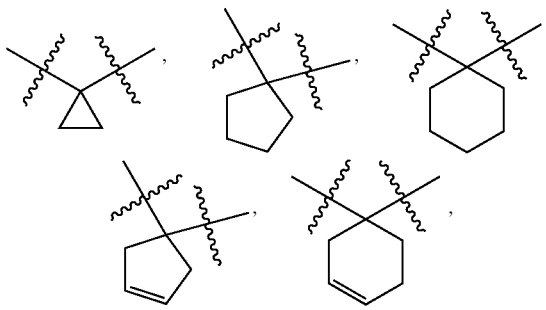

and the like.

"1-Alkylcyclopentylmethyl or -ethyl and 1-Alkylcyclohexylmethyl or -ethyl" means a radical having the formula:

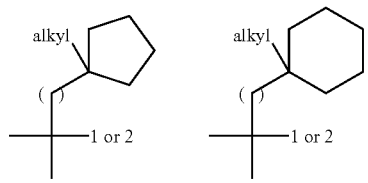

respectively; e.g., 1-methylcyclopentylmethyl, 1-methylcyclohexylmethyl, and the like "Disubstituted amino" refers to a —NRR' radical where R is alkyl, aryl, aralkyl, heteroaryl, heteroaralkyl, or heterocyclyl and R' is alkyl, aryl, aralkyl, heteroaryl, heteroaralkyl, cycloalkyl, heterocyclyl, cycloalkylalkyl, hydroxyalkyl, alkoxyalkyl, or acyl as defined herein. Representative examples include, but are not limited to, dimethylamino, methylphenylamino, benzylmethylamino, acetylmethylamino, and the like.

"Disease" specifically includes any unhealthy condition of an animal or part thereof and includes an unhealthy condition that may be caused by, or is incident to, medical or veterinary therapy applied to that animal, i.e., the "side effects" of such therapy.

"Deleterious immune response" means an immune response that prevents effective treatment of a patient or causes disease in a patient. As an example, dosing a patient with a murine antibody either as a therapy or as a diagnostic agent causes the production of human antimouse antibodies that prevent or interfere with subsequent treatments. The incidence of antibody formation versus pure murine monoclonals can exceed 70%. (see Khazaeli, M. B. et al. *J. Immunother.* 1994, 15, pp 42-52; Dillman R. O. et al. *Cancer Biother.* 1994, 9, pp 17-28; and Reinsberg, *J. Hybridoma.* 1995, 14, pp 205-208). Additional examples of known agents that suffer from deleterious immune responses are blood-clotting factors such as factor VIII. When administered to hemophilia A patients, factor VIII restores the ability of the blood to clot. Although factor VIII is a human protein, it still elicits an immune response in hemophiliacs as endogenous factor VIII is not present in their blood and thus it appears as a foreign antigen to the immune system. Approximately 29-33% of new patients will produce antibodies that bind and neutralize the therapeutically administered factor VIII (see Lusher *J. M. Semin Thromb Hemost.* 2002, 28(3), pp 273-276). These neutralizing antibodies require the administration of larger amounts of factor VIII in order to maintain normal blood clotting parameters; an expensive regimen of treatment in order to induce immune tolerance (see Briet E et al. *Adv. Exp. Med. Bio.* 2001, 489, pp 89-97). Another immunogenic example is adenoviral vectors. Retroviral therapy remains experimental and is of limited utility. One reason is that the application of a therapeutic virus generates an immune response capable of blocking any subsequent administration of the same or similar virus (see Yiping Yang et al. *J. of Virology.* 1995, 69, pp 2004-2015). This ensures that retroviral therapies must be based on the transient expression of a protein or the direct incorporation of viral sequence into the host genome. Directed research has identified multiple viral neutralizing epitopes recognized by host antibodies (see Hanne, Gahery-Segard et al. *J. of Virology* 1998. 72, pp 2388-2397) suggesting that viral modifications will not be sufficient to overcome this obstacle. This invention will enable a process whereby an adenoviral therapy will have utility for repeated application. Another example of an immunogenic agent that elicits neutralizing antibodies is the well-known cosmetic agent Botox. Botulin toxin protein, is purified from the fermentation of *Clostridium botulinum*. As a therapeutic agent, it is used for muscle disorders such as cervical dystonia in addition to cosmetic application. After repeated exposure patients generate neutralizing antibodies to the toxin, which results in reduced efficacy (see Birklein F. et al. *Ann Neurol.* 2002, 52, pp 68-73 and Rollnik, J. D. et al. *Neurol. Clin. Neurophysiol.* 2001, 2001(3), pp 2-4).

A "deleterious immune response" also encompasses diseases caused by therapeutic agents. A specific example of this is the immune response to therapy with recombinant human erythropoietin (EPO). Erythropoietin is used to stimulate the growth or red cells and restore red blood cell counts in patients who have undergone chemotherapy or dialysis. A small percentage of patients develop antibodies to EPO and subsequently are unresponsive to both therapeutically administered EPO and their own endogenous EPO (see Casadevall, N. et al., *NEJM.* 2002, 346, pp 469-475). They contract a disorder, pure red cell aplasia, in which red blood cell production is severely diminished (see Gershon S. K. et. al. *NEJM.* 2002, 346, pp 1584-1586). This complication of EPO therapy is lethal if untreated. Another specific example is the murine antibody OKT3 (a.k.a., Orthoclone), a monoclonal antibody directed towards CD-3 domain of activated T-cells. In clinical trials 20-40% of patients administered OKT3 produce antibodies versus the therapy. These antibodies, besides neutralizing the therapy, also stimulate a strong host immune reaction. The immune reaction is severe enough that patients with high titers of human anti-mouse antibodies are specifically restricted from taking the drug (see Orthoclone package label). Another example is a human antibody therapeutic. Humira® is a monoclonal antibody directed against TNF and is used to treat rheumatoid arthritis patients. When taken alone ~12% of patients develop neutralizing antibodies. In addition, a small percentage of patients given the drug also contract a systemic lupus erthematosus-like condition that is an IgG-mediated immune response induced by the therapeutic agent (see Humira package label). Another example of "deleterious immune response" is a host reaction to small molecule drugs. It is known to those skilled in the art that certain chemical structures will conjugate with host proteins to stimulate immune recognition (see Ju. C. et al. 2002, *Current Drug Metabolism* 3, pp 367-377 and Kimber I. et al. 2002, *Toxicologic Pathology* 30, pp 54-58.) A substantial portion of this host reactions are IgG mediated. Specific "deleterious immune responses" that are IgG mediated include, but are not limited to, hemolytic anemia, Steven-Johnson syndrome and drug-induced Lupus, "Four-atom heterocyclylalkylene" refers to a saturated divalent monocyclic radical of 4 carbon ring atoms wherein one of the ring carbon atoms is replaced by a heteroatom selected from —NR— where R is hydrogen, alkyl, acyl, alkylsulfonyl, aminosulfonyl, hydroxyalkyl, alkoxyalkyl, —O—, —S—, —SO—, or —S(O)$_2$—. Representative examples include, but are not limited to, rings such as:

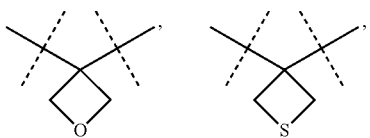

and the like.

"Halo" refers to fluoro, chloro, bromo or iodo.

"Haloalkyl" refers to alkyl as defined above substituted by one or more, preferably one to five, "halo" atoms, as such terms are defined in this Application. Haloalkyl includes monohaloalkyl, dihaloalkyl, trihaloalkyl, perhaloalkyl and the like, e.g. chloromethyl, dichloromethyl, difluoromethyl, trifluoromethyl, 2,2,2-trifluoroethyl, perfluoroethyl, 2,2,2-trifluoro-1,1-dichloroethyl, and the like.

"Haloalkoxy" refers to a —OR radical where R is haloalkyl group as defined above, e.g., trifluoromethoxy, 2,2,2-trifluoroethoxy, difluoromethoxy, and the like.

"Heteroaryl" as a group or part of a group denotes an aromatic monocyclic or multicyclic moiety of 5 to 10 ring atoms in which one or more, preferably one, two, or three, of the ring atom(s) is(are) selected from nitrogen, oxygen or sulfur, the remaining ring atoms being carbon. Representative heteroaryl rings include, but are not limited to, pyrrolyl, furanyl, thienyl, oxazolyl, isoxazolyl, thiazolyl, imidazolyl, triazolyl, tetrazolyl, pyridinyl, pyrimidinyl, pyrazinyl, pyridazinyl, indolyl, benzofuranyl, benzothienyl, benzimidazolyl, quinolinyl, isoquinolinyl, quinazolinyl, quinoxalinyl, pyrazolyl, and the like.

"Heteroaralkyl" refers to an -(alkylene)-R radical where R is heteroaryl as defined above, e.g., pyridinylmethyl, 1- or 2-furanylethyl, imidazolylmethyl, and the like, "Heteroaryloxyalkyl" refers to a -(alkylene)-OR radical where R is heteroaryl as defined above, e.g., furanyloxymethyl, 2- or 3-indolyloxyethyl, and the like.

"Heteroaryloxy" refers to a —OR radical where R is heteroaryl as defined above.

"Heteroaralkyloxy" refers to a —OR radical where R is heteroaralkyl as defined above.

"Heteroarylsulfonyl" refers to a —SO$_2$R radical where R is an heteroaryl group as defined above, e.g., pyridinylsulfonyl, and the like.

"Heterocyclyl" refers to a saturated or partially unsaturated, mono or bicyclic radical of 5 or 6 carbon ring atoms wherein one or more, preferably one, two, or three of the ring carbon atoms are replaced by a heteroatom selected from —N═, —N—, —O—, —S—, —SO—, or —S(O)$_2$— and further wherein one or two ring atoms are optionally replaced by a keto (—CO—) group. The heterocyclyl ring is optionally fused to cycloalkyl, aryl or heteroaryl ring as defined herein. Representative examples include, but are not limited to, imidazolidinyl, morpholinyl, thiomorpholinyl, thiomorpholino-1-oxide, thiomorpholino-1,1-dioxide, tetrahydropyranyl, tetrahydrothiopyranyl, 1-oxo-tetrahydrothiopyranyl, 1,1-dioxotetrathiopyranyl, indolinyl, piperazinyl, piperidyl, pyrrolidinyl, pyrrolinyl, quinuclidinyl, and the like.

"Heterocyclylalkyl" refers to an -(alkylene)-heterocyclyl radical as defined herein. Representative examples include, but are not limited to, imidazolidin-1-ylmethyl, morpholin-4-ylmethyl, thiomorpholin-4-ylmethyl, thiomorpholin-4-yl-methyl-1-oxide, indolinylethyl, piperazinylmethyl or ethyl, piperidylmethyl or ethyl, pyrrolidinylmethyl or ethyl, and the like.

"Heterocyclylalkylene" refers to a divalent heterocyclyl group, as defined herein, e.g., the instance wherein "$R^1$ and $R^2$ together with the carbon atom to which both $R^1$ and $R^2$ are attached form heterocyclylalkylene" includes, but is not limited to, the following:

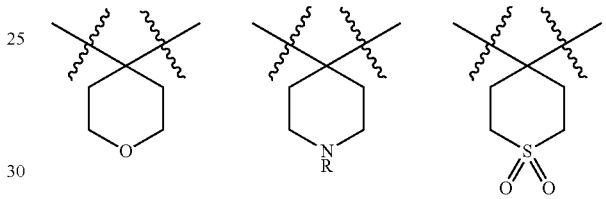

in which R is a substituent of a heterocyclyl group as disclosed herein.

"Hydroxy" means the —OH radical. Unless indicated otherwise, the compounds of the invention containing hydroxy radicals include protected derivatives thereof. Suitable protecting groups for hydroxy moieties include benzyl and the like.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkyloxy" or "hydroxyalkoxy" refers to a —OR radical where R is hydroxyalkyl as defined above, e.g., hydroxymethoxy, hydroxyethoxy, and the like.

"Isomers" mean compounds of Formula (I) having identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula (I) are meant to be encompassed all possible stereoisomers.

"Keto" or "oxo" means the (=O) radical.

"Monosubstituted amino" refers to a —NIH radical where R is alkyl, aryl, aralkyl, heteroaryl, heteroaralkyl, cycloalkyl, cycloalkylalkyl, hydroxyalkyl, alkoxyalkyl, or acyl as defined herein. Representative examples include, but are not limited to, methylamino, phenylamino, benzylamino, cycloalkylmethylamino, acetylamino, trifluoroacetyl, and the like.

"Nitro" means the —NO$_2$ radical.

"Optional" or "optionally" or "may be" means that the subsequently described event or circumstance may or may not occur, and that the description includes instances where the event or circumstance occurs and instances in which it does not. For example, the phrase "wherein the aromatic ring in $R^a$ is optionally substituted with one or two substituents independently selected from alkyl" means that the aromatic ring may or may not be substituted with alkyl in order to fall within the scope of the invention.

The present invention also includes N-oxide derivatives of a compound of Formula (I). "N-oxide derivative" mean a compound of Formula (I) in which a nitrogen atom is in an oxidized state (i.e., N→O), e.g., pyridine N-oxide, and which possesses the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula (I) which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methylsulfonic acid, ethanesulfonic acid, 1,2-ethanedisulfonic acid, 2-hydroxy-ethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

The present invention also includes prodrugs of a compound of Formula (I). "Prodrug" means a compound that is convertible in vivo by metabolic means (e.g. by hydrolysis) to a compound of Formula (I). For example, an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule. Suitable esters of compounds of Formula (I) containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methylsulphonates, ethanesulphonates, benzenesulphonates, p-toluenesulphonates, cyclohexylsulphamates and quinates. Suitable esters of compounds of Formula (I) containing a carboxy group are for example those described by Leinweber, F. J. *Drug Metab. Res.*, 1987, 18, page 379. An especially useful class of esters of compounds of Formula (I) containing a hydroxy group may be formed from acid moieties selected from those described by Bundgaard et al., *J. Med. Chem.*, 1989, 32, pp 2503-2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholinomethyl) benzoates, e.g. 3- or 4-(morpholinomethyl)-benzoates, and (4-alkylpiperazin-1-yl)benzoates, e.g. 3-OR$^4$-(4-alkylpiperazin-1-yl)benzoates.

"Protected derivatives" means derivatives of compounds of Formula (I) in which a reactive site or sites are blocked with protecting groups. Protected derivatives of compounds of Formula (I) are useful in the preparation of compounds of Formula (I) or in themselves may be active cysteine protease (such as Cathepsin S) inhibitors. A comprehensive list of suitable protecting groups can be found in T. W. Greene, *Protective Groups in Organic Synthesis,* 3rd edition, John Wiley & Sons, Inc. 1999.

The expression " . . . wherein the aromatic or alicyclic ring in $R^2$, $R^4$, or $R^6$ is optionally substituted with one to three $R^a$, $R^d$, or $R^e$, respectively . . . " refers to all the groups attached to $R^2$, $R^4$, or $R^6$ that contain an aromatic or alicyclic ring being optionally substituted with one to three $R^a$, $R^d$, or $R^e$ respectively. The aromatic or alicyclic ring may be directly attached to $R^2$, $R^4$, or $R^6$ or be part of a group that is directly attached to $R^2$, $R^4$, or $R^6$.

"Therapeutically effective amount" means that amount that, when administered to an animal for treating a disease, is sufficient to effect such treatment for the disease.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

"Treatment" or "treating" with respect to combination therapy (i.e., use with a biologic) means any administration of a compound of the present invention and includes:

(1) preventing the immune response from occurring in an animal which may be predisposed to the immune response but does not yet experience or display the pathology or symptomatology of the immune response;

(2) inhibiting the immune response in an animal that is experiencing or displaying the pathology or symptomatology of the immune response (i.e., arresting further development of the pathology and/or symptomatology); or (3) ameliorating the immune response in an animal that is experiencing or displaying the pathology or symptomatology of the immune response (i.e., reducing in degree or severity, or extent or duration, the overt manifestations of the immune response or reversing the pathology and/or symptomatology, e.g., reduced binding and presentation of antigenic peptides by MHC class II molecules, reduced activation of T-cells and B-cells, reduced humoral and cell-mediated responses and, as appropriate to the particular immune response, reduced inflammation, congestion, pain, necrosis, reduced loss in the efficacy of a biologic agent, and the like).

EMBODIMENTS OF THE INVENTION

In one particular aspect, the invention is directed to a compound of Formula (I) wherein:

$R^1$ is hydrogen or alkyl;

$R^2$ is hydrogen, alkyl, haloalkyl, carboxyalkyl, alkoxycarbonylalkyl, cycloalkyl, cycloalkylalkyl, aryl, aralkyl, heteroaryl, heteroaralkyl, heterocyclyl, heterocyclylalkyl, cyano, or -alkylene-X—$R^9$ (where X is —O—, —$NR^{10}$—, —$CONR^{11}$—, —$S(O)_{n1}$—, —$NR^{12}CO$—, —CO—, or —C(O)O— where n1 is 0-2, and $R^9$, $R^{10}$, $R^{11}$, and $R^{12}$ are independently hydrogen, alkyl, haloalkyl, cycloalkyl, cycloalkylalkyl, aryl, aralkyl, heteroaryl, or heteroaralkyl) wherein the aromatic or alicyclic ring in $R^2$ is optionally substituted with one, two, or three $R^a$ independently selected from alkyl, haloalkyl, alkoxy, hydroxy, haloalkoxy, halo, carboxy, alkoxycarbonyl, amino, monosubstituted amino, disubstituted amino, nitro, aryloxy, benzyloxy, acyl, or arylsulfonyl and further where the aromatic or alicyclic ring in $R^a$ is optionally substituted with one or two substituents independently selected from alkyl, halo, alkoxy, haloalkyl, haloalkoxy, hydroxy, amino, alkylamino, dialkylamino, carboxy, or alkoxycarbonyl; or $R^1$ and $R^2$ taken together with the carbon atom to which both $R^1$ and $R^2$ are attached form (i) cycloalkylene optionally substituted with one or two $R^b$ independently selected from alkyl, halo, alkylamino, dialkylamino, aryl, aralkyl, cycloalkyl, cycloalkylalkyl, heteroaryl, heteroaralkyl, alkoxycarbonyl, or aryloxycarbonyl;

or (iii) heterocyclylalkylene optionally substituted with one to four $R^c$ which are independently selected from alkyl, haloalkyl, hydroxy, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —$S(O)_{n2}R^{14}$, -alkylene-$S(O)_{n2}$—$R^{15}$, —$COOR^{16}$, -alkylene-$COOR^{17}$, —$CONR^{18}R^{19}$, or -alkylene-$CONR^{20}R^{21}$ (where n2 is 0-2 and $R^{14}$-$R^{18}$ and $R^{20}$ are independently hydrogen, alkyl, haloalkyl, aryl, aralkyl, heteroaryl, heteroaralkyl, cycloalkyl, cycloalkylalkyl, or heterocyclyl and $R^{19}$ and $R^{21}$ are independently hydrogen or alkyl);

wherein the aromatic or alicyclic ring in the groups attached to cycloalkylene or heterocyclylalkylene is optionally substituted with one, two, or three substituents independently selected from alkyl, haloalkyl, alkoxy, hydroxy, haloalkoxy, halo, carboxy, alkoxycarbonyl, amino, monsubstituted amino, disubstituted amino, or acyl;

$R^3$ is hydrogen or alkyl;

$R^5$ is hydrogen or alkyl;

$R^6$ is hydrogen, alkyl, haloalkyl, cycloalkyl, aryl, aralkyl, heteroaryl, heteroaralkyl, heterocyclyl, or -alkylene-$X^2$—$R^{25}$ (wherein $X^2$ is —$NR^{26}$—, —O—, —$S(O)_{n4}$—, —CO—, —COO—, —OCO—, —$NR^{26}CO$—, —$CONR^{26}$—, —$NR^{26}SO_2$—, —$SO_2NR^{26}$—, —$NR^{26}COO$—, —$OCONR^{26}$—, —$NR^{26}CONR^{27}$—, or —$NR^{26}SO_2NR^{27}$—, where $R^{26}$ and $R^{27}$ are independently hydrogen, alkyl, or acyl, n4 is 0-2, and $R^{25}$ is hydrogen, alkyl, haloalkyl, cycloalkyl, cycloalkylalkyl, heterocyclyl, heterocyclylalkyl, aryl, aralkyl, heteroaryl, or heteroaralkyl), wherein said alkylene chain in $R^6$ is optionally substituted with one to six halo and the aromatic or alicyclic ring in $R^6$ is optionally substituted with one, two, or three $R^e$ independently selected from alkyl, halo, hydroxy, alkoxy, haloalkyl, haloalkoxy, oxo, cyano, nitro, acyl, aryl, aralkyl, heteroaryl, heteroaralkyl, heterocyclyl, cycloalkyl, cycloalkylalkyl, carboxy, or alkoxycarbonyl, and further where the aromatic or alicyclic rings in $R^e$ is optionally substituted by one, two or three $R^f$ independently selected from alkyl, alkoxy, haloalkyl, haloalkoxy, halo, hydroxy, carboxy, cyano, nitro, aryl or cycloalkyl;

$R^7$ is haloalkyl;

$R^8$ is hydrogen, alkyl, alkoxyalkyl or haloalkyl; or $R^6$ and $R^8$ together with the carbon atom to which they are attached form cycloalkylene or heterocyclylalkylene wherein said cycloalkylene is optionally substituted with one or two substituents independently selected from alkyl, haloalkyl, hydroxy, or alkoxy and heterocyclylalkylene is optionally substituted with one or two substituents independently selected from alkyl, haloalkyl, hydroxy, or alkoxy;

$R^{22}$ is hydrogen, fluoro, alkyl, haloalkyl, cycloalkyl, cycloalkylalkyl, heterocyclyl, aryl, aralkyl, heteroaryl, heteroaralkyl, heterocyclyl, or heterocyclylalkyl, wherein the aromatic or alicyclic ring in $R^{22}$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or aryl;

Y is -alkylene- or -alkylene-O—, wherein the alkylene group is optionally substituted with one to six fluoro atoms; and Z is a direct bond, —O—, -alkylene- or —O-alkylene, wherein the alkylene portion is optionally substituted with one to six fluoro atoms;

or, a pharmaceutically acceptable salt thereof.

In another particular aspect, the invention is directed to a compound of Formula (I) wherein:

$R^1$ is hydrogen or alkyl;

$R^2$ is hydrogen, alkyl, haloalkyl, carboxyalkyl, alkoxycarbonylalkyl, cycloalkyl, cycloalkylalkyl, aryl, aralkyl, heteroaryl, heteroaralkyl, heterocyclyl, heterocyclylalkyl, cyano, -alkylene-X—$R^9$ (where X is —O—, —$NR^{10}$—, —$CONR^{11}$—, —$S(O)_{n1}$—, —$NR^{12}CO$—, —CO—, or —C(O)O— where n1 is 0-2, and $R^9$, $R^{10}$, $R^{11}$, and $R^{12}$ are independently hydrogen, alkyl, haloalkyl, cycloalkyl, cycloalkylalkyl, aryl, aralkyl, heteroaryl, or heteroaralkyl), wherein the aromatic or alicyclic ring in $R^2$ is optionally substituted with one, two, or three $R^a$ independently selected from alkyl, haloalkyl, alkoxy, hydroxy, haloalkoxy, halo, carboxy, alkoxycarbonyl, amino, monsubstituted amino, disubstituted amino, nitro, aryloxy, benzyloxy, acyl, or arylsulfonyl and further where the aromatic or alicyclic ring in $R^a$ is optionally substituted with one or two substituents independently selected from alkyl, halo, alkoxy, haloalkyl, haloalkoxy, hydroxy, amino, alkylamino, dialkylamino, carboxy, or alkoxycarbonyl; or $R^1$ and $R^2$ taken together with the carbon atom to which both $R^1$ and $R^2$ are attached form (i) cycloalkylene optionally substituted with one or two $R^b$ independently selected from alkyl, halo, alkylamino, dialkylamino, aryl, aralkyl, cycloalkyl, cycloalkylalkyl, heteroaryl, heteroaralkyl, alkoxycarbonyl, or aryloxycarbonyl;

or, (iii) heterocyclylalkylene optionally substituted with one to four $R^e$ which are independently selected from alkyl, haloalkyl, hydroxy, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —$S(O)_{n2}R^{14}$, -alkylene-$S(O)_{n2}$—$R^{15}$, —$COOR^{16}$, -alkylene-$COOR^{17}$, —$CONR^{18}R^{19}$, or -alkylene-$CONR^{20}R^{21}$ (where n2 is 0-2 and $R^{14}$-$R^{18}$ and $R^{20}$ are independently hydrogen, alkyl, haloalkyl, aryl, aralkyl, heteroaryl, heteroaralkyl, cycloalkyl, cycloalkylalkyl, or heterocyclyl and $R^{19}$ and $R^{21}$ are independently hydrogen or alkyl);

wherein the aromatic or alicyclic ring in the groups attached to cycloalkylene or heterocyclylalkylene is optionally substituted with one, two, or three substituents independently selected from alkyl, haloalkyl, alkoxy, hydroxy, haloalkoxy, halo, carboxy, alkoxycarbonyl, amino, monsubstituted amino, disubstituted amino, or acyl;

$R^3$ is hydrogen or alkyl;

$R^5$ is hydrogen or alkyl;

$R^6$ is hydrogen, alkyl, haloalkyl, cycloalkyl, aryl, aralkyl, heteroaryl, heteroaralkyl, heterocyclyl, or -alkylene-$X^2$—$R^{25}$ (wherein $X^2$ is —$NR^{26}$—, —O—, —$S(O)_m$—, —CO—, —COO—, —OCO—, —$NR^{26}CO$—, —$CONR^{26}$—, —$NR^{26}SO_2$—, —$SO_2NR^{26}$—, —$NR^{26}COO$—, —$OCONR^{26}$—, —$NR^{26}CONR^{27}$—, or —$NR^{26}SO_2NR^{27}$—, where $R^{26}$ and $R^{27}$ are independently hydrogen, alkyl, or acyl, n4 is 0-2, and $R^{25}$ is hydrogen, alkyl, haloalkyl, cycloalkyl, cycloalkylalkyl, heterocyclyl, heterocyclylalkyl, aryl, aralkyl, heteroaryl, or heteroaralkyl), wherein said alkylene chain in $R^6$ is optionally substituted with one to six halo and the aromatic or alicyclic rings in $R^6$ are optionally substituted by one, two, or three $R^e$ independently selected from alkyl, halo, hydroxy, alkoxy, haloalkyl, haloalkoxy, oxo, cyan, nitro, aryl, aralkyl, heteroaryl, heteroaralkyl, heterocyclyl, cycloalkyl, cycloalkylalkyl, carboxy, or alkoxycarbonyl and further where the aromatic or alicyclic rings in $R^e$ is optionally substituted by one, two or three $R^f$ independently selected from alkyl, alkoxy, haloalkyl, haloalkoxy, halo, hydroxy, carboxy, cyano, nitro, aryl or cycloalkyl;

$R^7$ is haloalkyl; and $R^8$ is hydrogen, alkyl, alkoxyalkyl or haloalkyl; or $R^6$ and $R^8$ together with the carbon atom to which they are attached form cycloalkylene or heterocyclylalkylene wherein said cycloalkylene is optionally substituted with one or two substituents independently selected from alkyl, haloalkyl, hydroxy, or alkoxy and heterocyclylalkylene is optionally substituted with one or two substituents independently selected from alkyl, haloalkyl, hydroxy, or alkoxy;

$R^{22}$ is hydrogen, fluoro, alkyl, haloalkyl, cycloalkyl, cycloalkylalkyl, heterocyclyl, aryl, aralkyl, heteroaryl, heteroaralkyl, heterocyclyl, or heterocyclylalkyl, wherein the aromatic or alicyclic ring in $R^{22}$ is optionally substituted with one, two, or three $R^d$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl;

Y is -alkylene- or -alkylene-O—, wherein the alkylene group is optionally substituted with one to six fluoro atoms; and Z is a direct bond or -alkylene- optionally substituted with one to six fluoro atoms; or, a pharmaceutically acceptable salt thereof.

A. One representative group of compounds is that of Formula (I) wherein $R^1$ and $R^2$ are hydrogen.

B. Another representative group of compounds is that of Formula (I) wherein $R^1$ and $R^2$ together with the carbon atom to which they are attached form cycloalkylene optionally substituted with one or two $R^b$ independently selected from alkyl, halo, dialkylamino, aryl, aralkyl, cycloalkyl, cycloalkylalkyl, heteroaryl, heteroaralkyl, alkoxycarbonyl, or aryloxycarbonyl; wherein the aromatic of alicyclic ring in the groups attached to cycloalkylene is optionally substituted with one, two, or three substituents independently selected from alkyl, haloalkyl, alkoxy, hydroxy, haloalkoxy, halo, carboxy, alkoxycarbonyl, amino, monsubstituted amino, disubstituted amino, or acyl. In one aspect, $R^1$ and $R^2$ together with the carbon atom to which they are attached form cyclopropylene, cyclobutylene, cyclopentylene, or cyclohexylene optionally substituted with groups described immediately above. In another aspect, $R^1$ and $R^2$ together with the carbon atom to which they are attached form cyclopropylene, cyclobutylene, cyclopentylene, cyclohexylene, cycloheptylene, 3-benzylcyclopentylene, 3-cyclohexylmethylcyclopentylene, 3-cyclopentylmethylcyclopentylene, 3-phenylcyclopentylene, 3-cyclohexylcyclopentylene, 3-cyclopentylcyclopentylene, 3-pyridin-2-ylmethylcyclopentylene, 3-pyridin-3-ylmethylcyclopentylene, 3-pyridin-4-ylmethylcyclopentylene, 2-methylcyclopropylene, 2,3-dimethylcyclopropylene, 3-benzylcyclobutylene, 3-methylcyclopentylene, 3,4-dimethylcyclopentylene, 3-ethylcyclopentylene, 3-(1,1-dimethylpropyl)-cyclopentylene, 3-n-butylcyclopentylene, 3-ethoxycarbonylcyclopentylene, 3,4-diethoxycarbonyl-cyclopentylene, or 3-benzyl-4-dimethylaminocyclopentylene. In a further aspect, $R^1$ and $R^2$ together with the carbon atom to which they are attached form cyclopropylene.

C. Yet another representative group of compounds is that of Formula (I) wherein $R^1$ and $R^2$ together with the carbon atom to which they are attached form heterocyclylalkylene optionally substituted with one to four $R^e$ which are independently selected from alkyl, haloalkyl, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —S(O)$_{n2}$R$^{14}$, -alkylene-S(O)$_{n2}$—R$^{15}$, —COOR$^{16}$, -alkylene-COOR$^{17}$, —CONR$^{18}$R$^{19}$, or -alkylene-CONR$^{20}$R$^{21}$ (where n2 is 0-2 and R$^{14}$-R$^{18}$ and R$^{20}$ are independently hydrogen, alkyl, haloalkyl, aryl, aralkyl, heteroaryl, heteroaralkyl, cycloalkyl, cycloalkylalkyl, or heterocyclyl and R$^{19}$ and R$^{21}$ are independently hydrogen or alkyl); wherein the aromatic or alicyclic ring in the groups attached to heterocyclylalkylene is optionally substituted with one, two, or three substituents independently selected from alkyl, haloalkyl, alkoxy, hydroxy, haloalkoxy, halo, carboxy, alkoxycarbonyl, amino, monsubstituted amino, disubstituted amino, or acyl. In one aspect, R$^1$ and R$^2$ together with the carbon atom to which they are attached form pyrrolidinyl, piperidinyl, tetrahydropyranyl, tetrahydrothiopyranyl, tetrahydrofuranyl, tetrahydrothiopyran-4-yl-1-oxide, tetrahydrothiopyran-4-yl-1,1-dioxide, hexahydropyrimidinyl, or hexahydropyridazinyl optionally substituted as described above. In another aspect, R$^1$ and R$^2$ together with the carbon atom to which they are attached form piperidin-4-yl substituted with one or two alkyl, haloalkyl, aminoalkyl, alkoxycarbonyl, alkoxyalkyl, alkoxyalkyloxyalkyl, heterocyclyl, heterocyclylalkyl, -alkylene-CONR$^{20}$R$^{21}$, or cycloalkyl. In a further aspect, R$^1$ and R$^2$ together with the carbon atom to which they are attached form piperidin-4-yl optionally substituted at the 1-position with methyl, ethyl, propyl, n-butyl, n-pentyl, 3-dimethylaminopropyl, 4-dimethylaminobutyl, 3-morpholin-4-ylpropyl, 3-piperidin-1-yl-propyl, 3-(4-methylpiperazin-1-yl)propyl, 3-(1-methylpiperidin-4-yl)propyl, 4-morpholin-4-ylbutyl, 2-(2-methoxyethyloxy)ethyl, 4-methoxybutyl, 4-aminocarbonylbutyl, 3-aminocarbonylpropyl, morpholin-4-yl, 4-methylpiperazin-1-yl, 1-ethoxycarbonylpiperidin-4-yl, 1,1-dioxotetrahydrothiopyran-4-yl, hydroxy, 2,2,2-trifluoroethyl, tert-butyl, 1,2-dimethylpiperidin-4-yl, 1,2,6-trimethylpiperidin-4-yl, 1,2,2-trimethylpiperidin-4-yl, 1-methyl-2-oxopiperidin-4-yl, 1-methylpiperidin-3-yl, 1-tert-butoxycarbonylpiperidin-4-yl, 1-cyclohexylpiperidin-4-yl, 1-cyclopropylmethylpyrrolidin-3-yl, 1-benzylpyrrolidin-3-yl, 1-benzyloxycarbonylpyrrolidin-3-yl, pyrrolidin-3-yl, 1-hydroxypyrrolidin-3-yl, 1-methylpyrrolidin-3-yl, 1-ethypyrrolidin-3-yl, 1-n-propyl or n-butylpyrrolidin-3-yl, 1-cyclohexylpyrrolidin-3-yl, 1-ethyl-2,2-dimethylpyrrolidin-4-yl, 1-propyl-2-methoxycarbonylpiperidin-4-yl, 2-oxopyrrolidin-3-yl, 1-ethyl-2-oxopyrrolidin-3-yl, morpholin-4-yl, 1-(1-methylpiperidin-4-ylcarbonyl)piperidin-4-yl, 1-ethoxycarbonylpiperidin-4-yl, 1-benzylazetidin-3-yl, tetrahydrothiopyran-4-yl-1-oxide, or tetrahydrothiopyran-4-yl-1,1-dioxide. In yet another aspect, R$^1$ and R$^2$ together with the carbon atom to which they are attached form piperidin-4-yl optionally substituted at the 1-position with methyl, ethyl, propyl, n-butyl, or 2,2,2-trifluoroethyl, tetrahydrothiopyran-4-yl, tetrahydrothiopyran-4-yl-1-oxide, tetrahydrothiopyran-4-yl-1,1-dioxide, or tetrahydropyran-4-yl.

(a) Within the above representative groups (A-C), an illustrative group of compounds is that wherein R$^3$ and R$^5$ are hydrogen; Y is -alkylene-; and Z is a direct bond. In one aspect, Y is methylene or ethylene. In another aspect, Y is methylene. Within this illustrative group, one embodiment of compounds of the invention is that wherein R$^{22}$ is fluoro, alkyl, aryl, aralkyl, cycloalkyl or cycloalkylalkyl.

(1) Within the above representative and illustrative groups, an exemplary group of compounds is that wherein R$^6$ is alkyl, haloalkyl, cycloalkyl, phenyl, benzyl, naphthyl, alkylSO$_2$alkyl, cycloalkylSO$_2$alkyl, aryl SO$_2$alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, thiazolyl, imidazolyl, pyridinyl, isoxazolyl, pyrimidinyl, pyrazinyl, pyridazinyl, indolyl, quinolinyl, benzofuranyl, benzthienyl, benzimidazolyl, benzthiazolyl, benzoisoxazolyl, benzoxazolyl or amino; wherein the aromatic or alicyclic ring in R$^6$ is optionally substituted by one, two, or three R$^e$, wherein each R$^e$ is independently alkyl, halo; hydroxy, oxo, carboxy, cyano, nitro, cycloalkyl, phenyl, naphthyl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyradinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl, quinoxalinyl, alkoxy, —COR (where R is alkyl), alkoxycarbonyl, aryloxycarbonyl where the aromatic or alicyclic rings in R$^e$ may be further optionally substituted by one, two or three R$^f$ independently selected from alkyl, alkoxy, haloalkyl, haloalkoxy, halo, hydroxy, carboxy, cyano, nitro, aryl or cycloalkyl.

In one aspect of the above, R$^6$ is methyl, ethyl, isopropyl, trifluoromethyl, cyclopropyl, cyclopentyl, cyclohexyl, phenyl, benzyl, naphthyl, pyrrolidinyl, piperidinyl, morpholinyl, thiomorpholinyl, piperazinyl, furanyl, thienyl, thiazolyl, imidazolyl, pyridinyl, or pyrazinyl wherein the aromatic or alicylic rings in R$^6$ are optionally substituted with one, two, or three R$^e$ independently selected from methyl, ethyl, fluoro, chloro, bromo, iodo, hydroxy, oxo, carboxy, cyano, nitro, cyclopropyl, phenyl, pyrrolidinyl, piperidinyl, morpholinyl, thiomorpholinyl, piperazinyl, thienyl, imidazolyl, methoxy, acetyl, or methoxycarbonyl, wherein the aromatic or alicyclic rings in R$^e$ are further optionally substituted with one, two, or three R$^f$ independently selected from methyl, cyclopropyl, phenyl, methoxy, fluoro, chloro, hydroxy, or carboxy. In one embodiment, R$^6$ is methyl.

In another aspect of the above, R$^6$ is phenyl, naphthyl, pyrrolidinyl, piperidinyl, morpholinyl, thiomorpholinyl, furanyl, thienyl, thiazolyl, imidazolyl, pyridinyl, or pyrazinyl wherein the aromatic or alicyclic rings in R$^6$ are optionally substituted with one, two, or three R$^e$ independently selected from methyl, fluoro, chloro, phenyl, thienyl, methoxy, acetyl, or methoxycarbonyl. In one embodiment, R$^6$ is phenyl, naphthyl, pyrrolidinyl, piperidinyl, furanyl, thienyl, thiazolyl, imidazolyl, pyridinyl, or pyrazinyl wherein the aromatic or alicyclic rings in R$^6$ are optionally substituted with one, two, or three R$^e$ independently selected from methyl, fluoro, chloro, phenyl, thienyl, methoxy, acetyl, or methoxycarbonyl. In another embodiment, R$^6$ is phenyl, 4-methoxyphenyl, 4-chlorophenyl, 4-fluorophenyl, 2-fluorophenyl, 2-fluoro-4-chlorophenyl, naphthyl, piperidin-4-yl, furanyl, thienyl, pyridin-4-yl, or pyrazinyl. In a further embodiment, R$^6$ is phenyl, 4-fluorophenyl, thiophen-2-yl, furan-2-yl, 2-hydroxyphenyl, 1-methylpyrrol-2-yl, or indol-3-yl, preferably, phenyl, 4-fluorophenyl, thiophen-2-yl, or furan-2-yl.

(2) Within the above representative and illustrative groups, a further exemplary group of compounds is that wherein R$^8$ is hydrogen or haloalkyl, preferably hydrogen or trifluoromethyl. In one embodiment of this exemplary group, R$^7$ is trifluoromethyl, 2,2,2-trifluoroethyl or pentafluoroethyl, preferably trifluoromethyl; and R$^8$ is hydrogen.

(3) Within the above representative and illustrative groups, a further exemplary group of compounds is that wherein R$^6$ and R$^8$ together with the carbon to which they are attached form cycloalkylene, preferably cyclopentylene, cyclopent-1-enylene, cyclohexylene, cyclohexlenylene. In one embodiment of this exemplary group, R$^7$ is trifluoromethyl, 2,2,2-trifluoroethyl or pentafluoroethyl, preferably trifluoromethyl (4) Within the above representative and illustrative groups, a further exemplary, group of compounds is that wherein $R^6$ and $R^8$ together with the carbon to which they are attached form heterocyclylalkylene, preferably tetrahydropyran-4-yl or 3,6-dihydro-2H-pyran-4-yl. In one embodiment of this exemplary group, $R^7$ is trifluoromethyl, 2,2,2-trifluoroethyl or pentafluoroethyl, preferably trifluoromethyl.

(5) Within the above representative and illustrative groups, a further exemplary group of compounds is that wherein $R^6$ is phenyl, naphthyl, pyrrolidinyl, piperidinyl, morpholinyl, thiomorpholinyl, furanyl, pyranyl, thienyl, thiazolyl, imidazolyl, pyridinyl, or pyrazinyl wherein the aromatic or alicyclic rings in $R^6$ are optionally substituted with one, two, or three $R^e$ independently selected from methyl, fluoro, chloro, phenyl, thienyl, methoxy, acetyl, or methoxycarbonyl. Most preferably, $R^6$ is phenyl, 4-methoxyphenyl, 4-chlorophenyl, 4-fluorophenyl, 2-fluorophenyl, 2-fluoro-4-chlorophenyl, naphthyl, piperidin-4-yl, furanyl, thienyl, pyridin-4-yl, or pyrazinyl. In one embodiment of this exemplary group, $R^7$ is trifluoromethyl, 2,2,2-trifluoroethyl or pentafluoroethyl, preferably trifluoromethyl; and $R^3$, $R^5$, and $R^8$ are hydrogen.

Reference to the embodiments set forth above is meant to include all combinations of representative, illustrative and exemplary groups unless stated otherwise.

Compounds of this invention can be made by the methods depicted in the reaction schemes shown below. These schemes are merely illustrative of some methods by which the compounds of this invention can be synthesized, and various modifications to these schemes can be made and will be suggested to one skilled in the art having referred to this disclosure.

The starting materials and reagents used in preparing these compounds are either available from commercial suppliers such as, e.g., Aldrich Chemical Co., (Milwaukee, Wis.), Bachem (Torrance, Calif.), or Sigma (St. Louis, Mo.), or are prepared by methods known to those skilled in the art following procedures set forth in references such as Fieser and Fieser's *Reagents for Organic Synthesis*, Volumes 1-17 (John Wiley and Sons, 1991); Rodd's *Chemistry of Carbon Compounds*, Volumes 1-5 and Supplementals (Elsevier Science Publishers, 1989); *Organic Reactions*, Volumes 1-40 (John Wiley and Sons, 1991), March's *Advanced Organic Chemistry*, (John Wiley and Sons, 4th Edition) and Larock's *Comprehensive Organic Transformations* (VCH Publishers Inc., 1989).

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C., and most preferably at about room (or ambient) temperature, e.g., about 20° C.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *"Protective Groups in Organic Chemistry"* John Wiley and Sons, 1999.

Compounds of Formula (I) where $R^1$, $R^2$, $R^3$, $R^5$, $R^6$, $R^7$, $R^{22}$, Y and Z are as defined herein and $R^8$ is hydrogen can be prepared by proceeding as in the following Reaction Scheme 1 below.

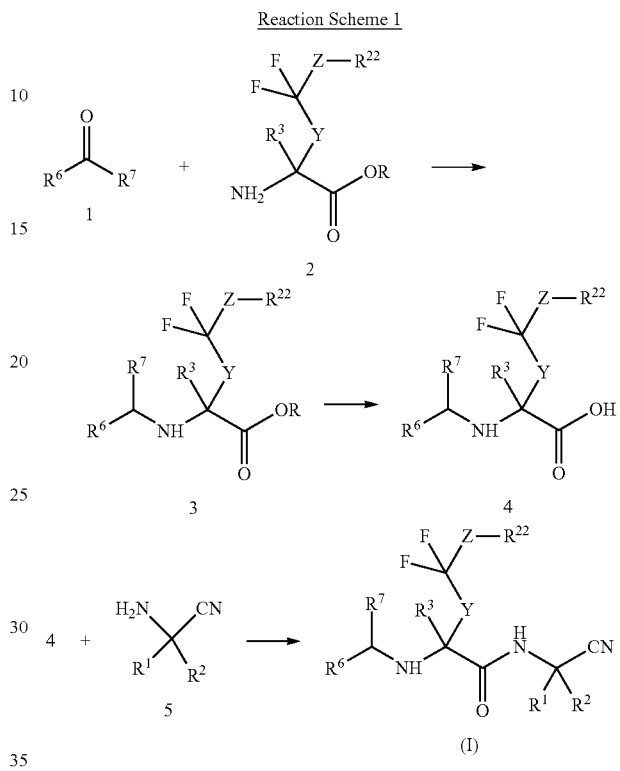

Reaction Scheme 1

Reaction of a ketone of formula 1 with an α-amino ester of formula 2 where R is a carboxy protecting group, preferably an alkyl group, preferably methyl, under reductive amination reaction conditions provide a compound of formula 3. The reaction is carried out in the presence of a suitable dehydrating agent such as $TiCl_4$, magnesium sulfate, isopropyl trifluoroacetate, in the presence of a base such as diisopropylethylamine, pyridine, and the like and in a suitable organic solvent such as methylene chloride to give an imine. The imine is reduced with a suitable reducing agent such as sodium borohydride, sodium cyanoborohydride, and the like in a suitable organic solvent such as methanol, ethanol, and the like.

Compound 4 is then reacted with an α-aminoacetonitrile of formula 5 to give a compound of Formula (I). The reaction is typically carried out in the presence of a suitable coupling agent (such as for example, benzotriazole-1-yloxytrispyrrolidinophosphonium hexafluorophosphate (PyBOP®), O-benzotriazol-1-yl-N,N,N',N'-tetramethyl-uronium hexafluorophosphate (EBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (BDC), or 1,3-dicyclohexyl-carbodiimide (DCC)), optionally in the presence of 1-hydroxybenzotriazole (HOST), and a base such as N,N-diisopropylethylamine, triethylamine, N-methylmorpholine, and the like. The reaction is typically carried out at about 20 to about 30° C., preferably at about 25° C., and normally requires about 2 to about 24 h to complete. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like.

Alternatively, the above coupling step can be carried out by first converting 4 into an active acid derivative such as succinimide ester and then reacting it with an amine of formula 5. The reaction typically requires about 2 to about 3 h to complete. The conditions utilized in this reaction depend on the nature of the active acid derivative. For example, if it is an acid chloride derivative of 4, the reaction is carried out in the presence of a suitable base (e.g. triethylamine, diisopropylethylamine, pyridine, and the like). Suitable reaction solvents are polar organic solvents such as acetonitrile, N,N-dimethylformamide, dichloromethane, or any suitable mixtures thereof.

The above method can also be used to prepare compounds of Formula (I) where $R^8$ is other than hydrogen utilizing the procedure described in method (i) above, by substituting $R^6COH$ with a ketone of formula $R^6R^7CO$ and then treating the resulting intermediate with $R^8Li/R^8MgX$, followed by oxidation to give the free acid. The free acid is then condensed with 5 under conditions described above to give compound (I).

It will be apparent to a person skilled in the art, that compounds of Formula (I) can also be prepared by first condensing 5 with the N-protected amino acid of formula 2 where R is hydrogen, followed by removal of the amino protecting group and reaction of the free amino compound with a compound of formula 1 as described in Scheme 1 above. Suitable amino acid protecting groups and reaction conditions for putting them on and removing them can be found in Greene, T. W.; and Wuts, P. G. M.; *Protecting Groups in Organic Synthesis*; John Wiley & Sons, Inc. 1999.

Compounds of formula 1 such as 2,2,2-trifluoromethylacetophenone and 2,2,2-trifluoromethyl-4-phenylphenylethanone are commercially available. Others can be prepared by methods well known in the art. α-Amino esters of formula 2 may be commercially available or they can be prepared by methods well known in the art. For example, compounds of formula 2 can be prepared as shown below in Method (i).

Method (i)

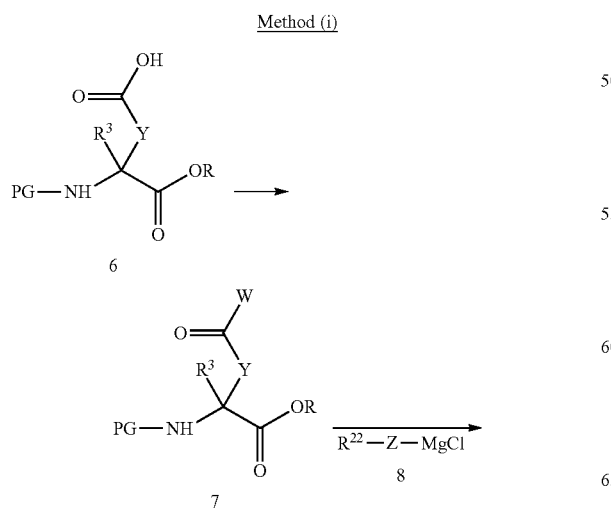

An α-amino ester of formula 6, where PG is a protecting group (such as, e.g., Boc), is halogenated (formula 7, W=Br, Cl or I) and is then reacted with a substituted magnesium chloride of formula 8 to give the substituted amino ester of formula 9, which in turn is difluorinated by reaction with a source of fluorine atoms, such as for example (diethylamino) sulfur trifluoride (DAST) or Deoxofluor. The resulting difluoro compound of formula 10 is then deprotected to give the α-amino ester of formula 2 or a salt thereof.

Alternatively, compounds of formula 2 can be prepared as shown below in Method (ii).

Method (ii)

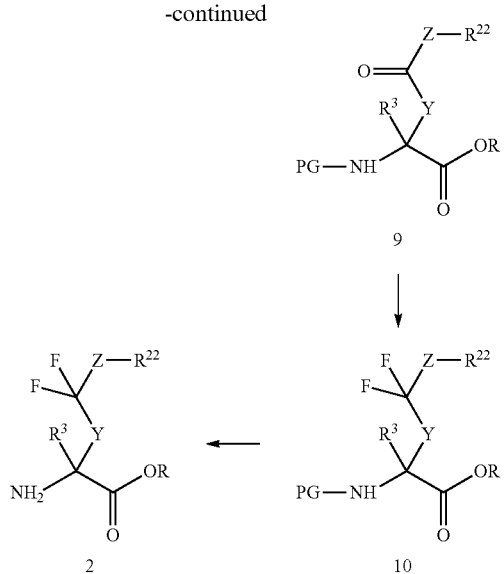

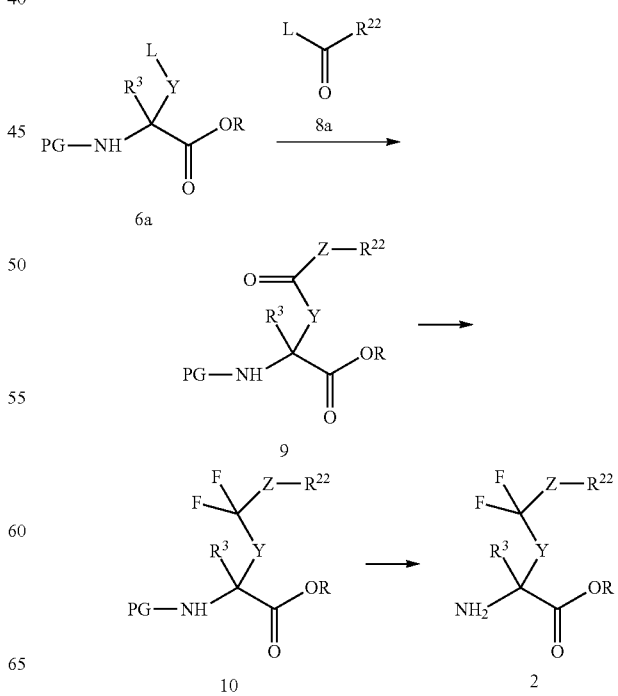

An α-amino ester of formula 6a, where PG is a protecting group (such as, e.g., Boc), is halogenated (formula 7, L=Br, Cl or I) and is then reacted with a carboxylic acid derivative of formula 8a to give the substituted amino ester of formula 9, which in turn is difluorinated by reaction with a source of fluoro atoms, such as for example (diethylamino)sulfur trifluoride (DAST) or Deoxofluor. The resulting difluoro compound of formula 10 is then deprotected to give the α-amino ester of formula 2 or a salt thereof.

A compound of Formula (I) can be converted to other compounds of Formula (I). For example:

A compound of Formula (I) where $R^6$ is an aromatic ring substituted with halo can be reacted with appropriate boronic acid-under-palladium catalyzed Suzuki coupling reaction conditions to provide a corresponding compound of Formula (I) where $R^6$ is further substituted with an aryl or heteroaryl ring.

A compound of Formula (I) containing a hydroxy group may be prepared by dealkylation/benzylation of an alkoxy/benzyloxy substituent: those containing an acid group, by hydrolysis of an ester group; and those containing a cyano, by displacement of a bromine atom on the corresponding compounds of Formula (I). A compound of Formula (I) containing a halo group such as chloro can be converted to a corresponding compound of Formula (I) containing an methylthio by treating it with sodium thiomethoxide. The methylthio group can be oxidized to methylsulfonyl using a suitable oxidizing agent such as OXONE®. A compound of Formula (I) containing a cyano group can be converted to a corresponding carboxy-containing compound by hydrolysis of the cyano group. The carboxy group, in turn, can be converted to an ester group.

A compound of Formula (I) can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula (I) can be prepared by reacting the free acid form of the compound with a pharmaceutically acceptable inorganic or organic base. Inorganic and organic acids and bases suitable for the preparation of the pharmaceutically acceptable salts of compounds of Formula (I) are set forth in the definitions section of this Application. Alternatively, the salt forms of the compounds of Formula (I) can be prepared using salts of the starting materials or intermediates.

The free acid or free base forms of the compounds of Formula (I) can be prepared from the corresponding base addition salt or acid addition salt form. For example, a compound of Formula (I) in an acid addition salt form can be converted to the corresponding free base by treating with a suitable base (e.g., ammonium hydroxide solution, sodium hydroxide, and the like). A compound of Formula (I) in a base addition salt form can be converted to the corresponding free acid by treating with a suitable acid (e.g., hydrochloric acid, etc).

The N-oxides of compounds of Formula (I) can be prepared by methods known to those of ordinary skill in the art. For example, N-oxides can be prepared by treating an unoxidized form of the compound of Formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formula (I) can be prepared from the N-oxide of an appropriate starting material.

Compounds of Formula (I) in unoxidized form can be prepared from N-oxides of compounds of Formula (I) by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at about 0 to about 80° C.

Prodrug derivatives of the compounds of Formula (I) can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound of Formula (I) with a suitable carbamylating agent (e.g., 1,1-acyloxyalkylcarbonochloridate, para-nitrophenyl carbonate, or the like).

Protected derivatives of the compounds of Formula (I) can be made by means known to those of ordinary skill in the art. A detailed description of the techniques applicable to the creation of protecting groups and their removal can be found in T. W. Greene, *Protecting Groups in Organic Synthesis*, $3^{rd}$ edition, John Wiley & Sons, Inc. 1999.

Compounds of the present invention may be conveniently prepared or formed during the process of the invention as solvates (e.g. hydrates). Hydrates of compounds of the present invention may be conveniently prepared by recrystallisation from an aqueous/organic solvent mixture, using organic solvents such as dioxin, tetrahydrofuran or methanol.

Compounds of Formula (I) can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula (I), dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

In practicing this invention several processes for the generation or purification of biological agents are used. Methods for preparing the biologics are well known in the art as discussed below.

Monoclonal antibodies are prepared using standard techniques, well known in the art, such as by the method of Kohler and Milstein, *Nature* 1975, 256:495, or a modification thereof, such as described by Buck et al. 1982, *In Vitro* 18:377. Typically, a mouse or rat is immunized with the MenB PS derivative conjugated to a protein carrier, boosted and the spleen (and optionally several large lymph nodes) removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and will not be rinsed away with the rest of the suspension. Resulting B-cells, or all dissociated spleen cells, are then induced to fuse with myeloma cells to form hybridomas. Representative murine myeloma lines for use in the hybridizations include those available from the American Type Culture Collection (ATCC).

Chimeric antibodies composed of human and non-human amino acid sequences may be formed from the mouse monoclonal antibody molecules to reduce their immunogenicity in humans (Winter et al. *Nature* 1991 349:293; Lobuglio et al. *Proc. Nat. Acad. Sci. USA* 1989 86:4220; Shaw et al. *J. Immunol.* 1987 138:4534; and Brown et al. *Cancer Res.* 1987 47:3577; Riechmann et al. *Nature* 1988 332:323; Verhoeyen et al. *Science* 1988 239:1534; and Jones et al. *Nature* 1986 321:522; EP Publication No. 519,596, published Dec. 23, 1992; and U.K. Patent Publication No. GB 2,276,169, published Sep. 21, 1994).

Antibody molecule fragments, e.g., F(ab')$_2$, FV, and sFv molecules, that are capable of exhibiting immunological binding properties of the parent monoclonal antibody molecule can be produced using known techniques. Inbar et al. *Proc. Nat. Acad. Sci. USA* 1972 69:2659; Hochman et al. *Biochem.* 1976 15:2706; Ehrlich et al. *Biochem.* 1980 19:4091; Huston et al. *Proc. Nat. Acad. Sci. USA* 1988 85(16):5879; and U.S. Pat. Nos. 5,091,513 and 5,132,405, and U.S. Pat. No. 4,946,778.

In the alternative, a phage-display system can be used to expand the monoclonal antibody molecule populations in vitro. Saiki, et al. *Nature* 1986 324:163; Scharf et al. *Science* 1986 233:1076; U.S. Pat. Nos. 4,683,195 and 4,683,202; Yang et al. *J. Mol. Biol.* 1995 254:392; Barbas, III et al. *Methods: Comp. Meth Enzymol.* 1995 8:94; Barbas, III et al. *Proc. Natl. Acad. Sci. USA* 1991 88:7978.

The coding sequences for the heavy and light chain portions of the Fab molecules selected from the phage display library can be isolated or synthesized, and cloned into any suitable vector or replicon for expression. Any suitable expression system can be used, including, for example, bacterial, yeast, insect, amphibian and mammalian systems. Expression systems in bacteria include those described in Chang et al. *Nature* 1978 275:615, Goeddel et al. *Nature* 1979 281:544, Goeddel et al. *Nucleic Acids Res.* 1980 8:4057, European Application No. EP 36,776, U.S. Pat. No. 4,551,433, deBoer et al. *Proc. Natl. Acad. Sci. USA* 1983 80:21-25, and Siebenlist et al. *Cell* 1980 20:269.

Expression systems in yeast include those described in Hinnen et al. *Proc. Natl. Acad. Sci. USA* 1978 75:1929, Ito et al. *J. Bacteriol.* 1983 153:163, Kurtz et al. *Mol. Cell. Biol.* 1986 6:142, Kunze et al. *J. Basic Microbiol.* 1985 25:141, Gleeson et al. *J. Gen. Microbiol.* 1986 132:3459, Roggenkamp et al. *Mol. Gen. Genet.* 1986 202:302, Das et al. *J. Bacteriol.* 1984 158:1165, De Louvencourt et al. *J. Bacteriol.* 1983 154:737, Van den Berg et al. *Bio/Technology* 1990 8:135, Kunze et al. *J. Basic Microbiol.* 1985 25:141, Cregg et al. *Mol. Cell. Biol.* 1985 5:3376, U.S. Pat. Nos. 4,837,148 and 4,929,555, Beach et al. *Nature* 1981 300:706, Davidow et al. *Curr. Genet.* 1985 10:380, Gaillardin et al. *Curr. Genet.* 1985 10:49, Ballance et al. *Biochem. Biophys. Res. Commun.* 1983 112:284-289, Tilburn et al. *Gene* 1983 26:205-221, Yelton et al. *Proc. Natl. Acad. Sci. USA* 1984 81:1470-1474, Kelly et al. *EMBO J.* 1985 4:475479; European Application No. EP 244, 234, and International Publication No. WO 91/00357.

Expression of heterologous genes in insects can be accomplished as described in U.S. Pat. No. 4,745,051, European Application Nos. EP 127,839 and EP 155,476, Vlak et al, *J. Gen. Virol.* 1988 69:765-776, Miller et al. *Ann. Rev. Microbiol.* 1988 42:177, Carbonell et al. *Gene* 1988 73:409, Maeda et al. *Nature* 1985 315:592-594, Lebacq-Verheyden et al. *Mol. Cell. Biol.* 1988 8:3129, Smith et al. *Proc. Natl. Acad. Sci. USA* 1985 82:8404, Miyajima et al. *Gene* 1987 58:273, and Martin et al. *DNA* 1988 7:99. Numerous baculoviral strains and variants and corresponding permissive insect host cells from hosts are described in Luckow et al. *Bio/Technology* 1988 6:47-55, Miller et al. *GENETIC ENGINEERING*, Setlow, J. K. et al. eds., Vol. 8, Plenum Publishing, pp. 1986 277-279, and Maeda et al. *Nature* 1985 315:592-594.

Mammalian expression can be accomplished as described in Dijkema et al. *EMBO J.* 1985 4:761, Gorman et al. *Proc. Natl. Acad. Sci. USA* 1982 79:6777, Boshart et al. *Cell* 1985 41:521, and U.S. Pat. No. 4,399,216. Other features of mammalian expression can be facilitated as described in Ham et al. *Meth. Enz.* 1979 58:44, Barnes et al. Anal. Biochem. 1980 102:255, U.S. Pat. Nos. 4,767,704, 4,657,866, 4,927,762, 4,560,655 and Reissued U.S. Pat. No. RE 30,985, and in International Publication Nos. WO 90/103430, WO 87/00195. The production of recombinant adenoviral vectors are described in U.S. Pat. No. 6,485,958. Botulinum toxin type A can be obtained by establishing and growing cultures of *Clostridium botulinum* in a fermenter and then harvesting and purifying the fermented mixture in accordance with known procedures. Any of the above-described protein production methods can be used to provide the biologic that would benefit from the present invention.

The compounds of the invention are selective inhibitors of cysteine proteases such as Cathepsin S, K, B, and/or F, and in particular Cathepsin S, and accordingly are useful for treating diseases in which cysteine protease activity contributes to the pathology and/or symptomatology of the disease. For example, the compounds of the invention are useful in treating autoimmune disorders, including, but not limited to, juvenile onset diabetes, psoriasis, multiple sclerosis, pemphigus vulgaris, Graves' disease, myasthenia gravis, systemic lupus erythemotasus, rheumatoid arthritis and Hashimoto's thyroiditis; allergic disorders, including, but not limited to, asthma; and allogeneic immune responses, including, but not limited to, organ transplants or tissue grafts and endometriosis.

Cathepsin S is also implicated in disorders involving excessive elastolysis, such as chronic obstructive pulmonary disease (e.g., emphysema), bronchiolitis, excessive airway elastolysis in asthma and bronchitis, pneumonities and cardiovascular disease such as plaque rupture and atheroma. Cathepsin S is implicated in fibril formation and, therefore, inhibitors of Cathepsin S are of use in treatment of systemic amyloidosis.

The cysteine protease inhibitory activities of the compounds of Formula (I) can be determined by methods known to those of ordinary skill in the art. Suitable in vitro assays for measuring protease activity and the inhibition thereof by test compounds are known. Typically, the assay measures protease-induced hydrolysis of a peptide-based substrate.

Details of assays for measuring protease inhibitory activity are set forth in Biological Examples 1-5, infra.

In general, compounds of Formula (I) will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula (I) may range from about 10 micrograms per kilogram body weight (μg/kg) per day to about 100 milligram per kilogram body weight (mg/kg) per day, typically from about 100 μg/kg/day to about 10 mg/kg/day. Therefore, a therapeutically effective amount for an 80 kg human patient may range from about 1 mg/day to about 8 g/day, typically from about 1 mg/day to about 800 mg/day. In general, one of ordinary skill in the art, acting in reliance upon personal knowledge and the disclosure of this Application, will be able to ascertain a therapeutically effective amount of a compound of Formula (I) for treating a given disease.

The compounds of Formula (I) can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula (I) in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula (I) in the composition may vary widely depending upon the type of formulation, size of a unit dosage, kind of excipients and other factors known to those of skill in the art of pharmaceutical sciences. In general, a composition of a compound of Formula (I) for treating a given disease will comprise from 0.01% w to 10% w, preferably 0.3% w to 1% w of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula (I) are described in the Formulation Examples below.

SYNTHESIS EXAMPLES

The present invention is further exemplified, but not limited by, the following examples that illustrate the preparation of compounds of Formula (I) and intermediates according to the invention.

Synthesis Example 1

Scheme 1

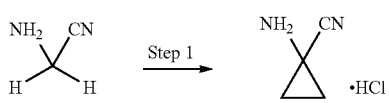

Scheme 1, Step 1: Synthesis of 1-aminocyclopropanecarbonitrile hydrochloride (1-aminocyclopropanecarbonitrile hydrochloride is commercially available)

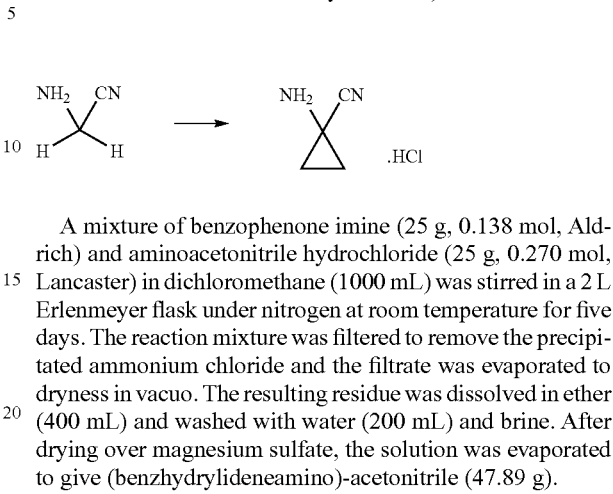

A mixture of benzophenone imine (25 g, 0.138 mol, Aldrich) and aminoacetonitrile hydrochloride (25 g, 0.270 mol, Lancaster) in dichloromethane (1000 mL) was stirred in a 2 L Erlenmeyer flask under nitrogen at room temperature for five days. The reaction mixture was filtered to remove the precipitated ammonium chloride and the filtrate was evaporated to dryness in vacuo. The resulting residue was dissolved in ether (400 mL) and washed with water (200 mL) and brine. After drying over magnesium sulfate, the solution was evaporated to give (benzhydrylideneamino)-acetonitrile (47.89 g).

A solution of sodium hydroxide (91 g, 2.275 mol) in water (91 mL) in a 2 L flask was cooled on ice under nitrogen and then treated with benzyl triethyl ammonium chloride (2.0 g, 0.0088 mol, Aldrich) and (benzhydrylideneamino)acetonitrile (47.89 g) in toluene (100 mL). 1,2-Dibromoethane (23 mL, 122.4 mmol, Aldrich) was then added dropwise, over 25 min, to the reaction mixture with mechanical stirring and cooling to maintain the internal temperature near +10° C. The reaction mixture was then stirred vigorously for 24 hr at room temperature and then poured into ice water and extracted with toluene. The combined extracts were washed with brine and then treated with MgSO$_4$ and Norite. After filtering, toluene was removed by rotary evaporation to give an oil (67 g). The residue was dissolved in boiling hexane (400 mL), treated with Norite and filtered hot and allowed to cool. A dark oil separated, which was removed by pipet (~2 mL). Scratching induced crystallization in the remaining solution, which was cooled on ice for 2 hr. Light yellow crystals were collected by filtration and washed with cold hexane to give 1-(benzhydrylideneamino)-cyclopropanecarbonitrile (30.56 g).

A mixture of 1-(benzhydrylideneamino)cyclopropanecarbonitrile (30.56 g, 0.124 mol) in concentrated HCl (12 mL) in water (100 mL) and ether (100 mL) was stirred at room temperature for 15 hr. The ether layer was discarded and the aqueous layer was washed with ether. The aqueous layer was then freeze-dried to give 1-aminocyclopropanecarbonitrile hydrochloride as a tan powder (13.51 g). Analytical data is consistant with published data.

Synthesis Example 2

Scheme 2

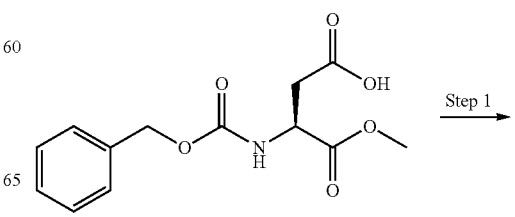

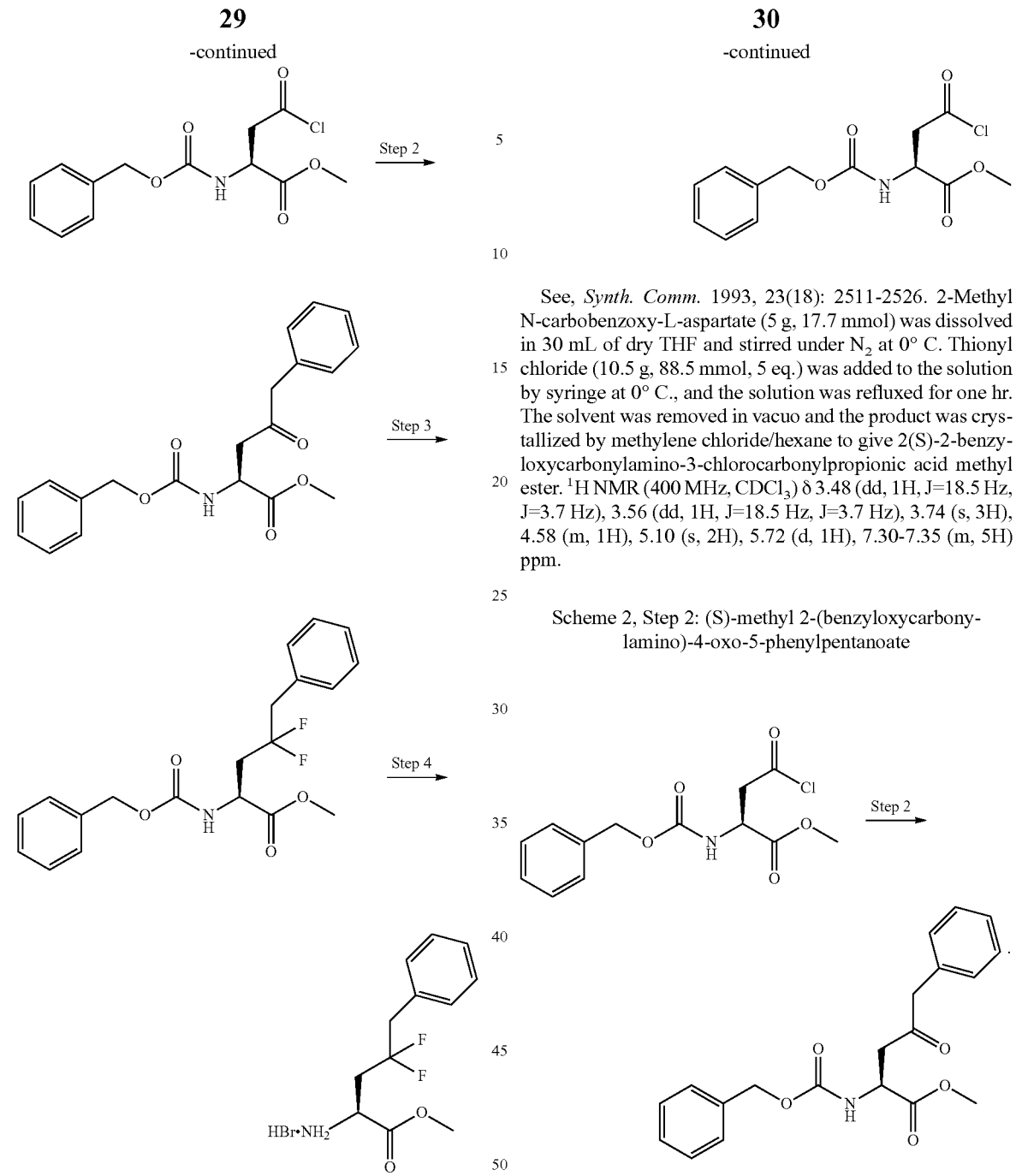

See, *Synth. Comm.* 1993, 23(18): 2511-2526. 2-Methyl N-carbobenzoxy-L-aspartate (5 g, 17.7 mmol) was dissolved in 30 mL of dry THF and stirred under $N_2$ at 0° C. Thionyl chloride (10.5 g, 88.5 mmol, 5 eq.) was added to the solution by syringe at 0° C., and the solution was refluxed for one hr. The solvent was removed in vacuo and the product was crystallized by methylene chloride/hexane to give 2(S)-2-benzyloxycarbonylamino-3-chlorocarbonylpropionic acid methyl ester. $^1$H NMR (400 MHz, $CDCl_3$) δ 3.48 (dd, 1H, J=18.5 Hz, J=3.7 Hz), 3.56 (dd, 1H, J=18.5 Hz, J=3.7 Hz), 3.74 (s, 3H), 4.58 (m, 1H), 5.10 (s, 2H), 5.72 (d, 1H), 7.30-7.35 (m, 5H) ppm.

Scheme 2, Step 2: (S)-methyl 2-(benzyloxycarbonylamino)-4-oxo-5-phenylpentanoate To a suspension of copper(I) bromide-dimethyl sulfide complex (2.6 g, 12.72 mmol, 1.2 eq.) in dry THF was added a solution of lithium bromide (2.2 g, 25.44 mmol, 2.4 eq.) in dry THF. The mixture was stirred at room temperature (RT) for 20 min, and then was cooled to −78° C. A solution of benzyl magnesium chloride (13 mL, 12.72 mmol, 1.2 eq.) followed by a solution of (S)-methyl 2-(benzyloxycarbonylamino)-4-chloro-4-oxobutanoate (3.16 g, 10.6 mmol, 1 eq.) in dry THF were added. The mixture was stirred at −78° C. for 30 min and then was quenched with sat. ammonium chloride. The mixture was extracted with ethyl acetate. The organic layers were dried over magnesium sulfate and then concentrated in vacuo. The residue was purified by flash column (1:1 ethyl acetate:hexane) to give 2 g of (S)-methyl 2-(benzyloxycarbonylamino)-4-oxo-5-phenylpentanoate.

Scheme 2, Step 1: Synthesis of (S)-methyl 2-(benzyloxycarbonylamino)-4-chloro-4-oxobutanoate

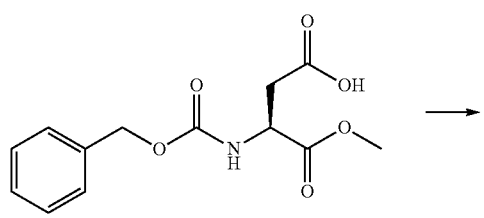

Scheme 2, Step 3: (S)-methyl 2-(benzyloxycarbonylamino)-4,4-difluoro-5-phenylpentanoate

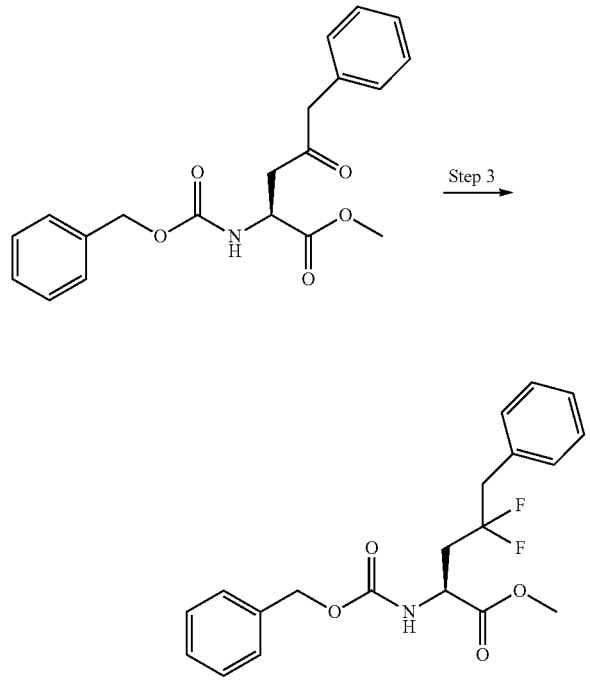 [SMILES: COC(=O)[C@H](CC(=O)Cc1ccccc1)NC(=O)OCc1ccccc1 ; COC(=O)[C@H](CC(F)(F)Cc1ccccc1)NC(=O)OCc1ccccc1]

A mixture of (S)-methyl 2-(benzyloxycarbonylamino)-4-oxo-5-phenylpentanoate (2 g) and (diethylamino)sulfur trifluoride (DAST) (5 g) was stirred at RT over three days. The mixture was then diluted with dichloromethane (100 mL) and carefully added to 0.5N NaOH solution (150 mL). The aqueous layer was extracted with methylene chloride. The organic layers were dried over magnesium sulfate and were then concentrated in vacuo. The residue was purified by flash column (1:4-1:3 ethyl acetate:hexane) to give (S)-methyl 2-(benzyloxycarbonylamino)-4,4-difluoro-5-phenylpentanoate. $^1$H-NMR (CDCl$_3$) δ 7.2-7.4 (4H, m), 5.4 (1H), 5.05 (2H), 4.6 (1H), 3.7 (3H), 3.15 (2H), 2.3 (2H). $^{19}$F-NMR (CDCl$_3$) δ −95 ppm.

Scheme 2, Step 4: (S)-Methyl 2-amino-4,4-difluoro-5-phenylpentanoate hydrobromide

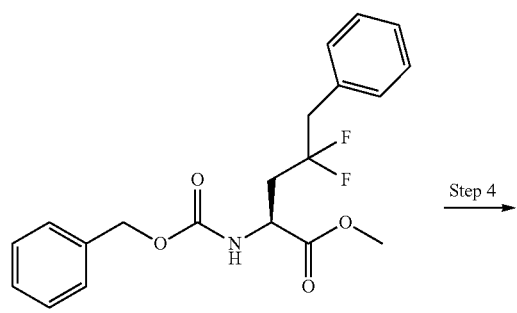

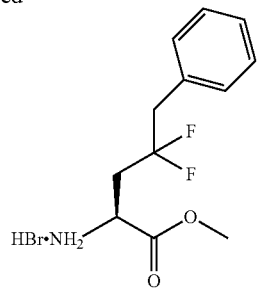

A mixture of (S)-methyl 2-(benzyloxycarbonylamino)-4,4-difluoro-5-phenylpentanoate (188 mg, 0.5 mmol) and hydrogen bromide (2 mL) was stirred at RT for two hr, after which the solvent was removed to give the title (S)-methyl 2-amino-4,4-difluoro-5-phenylpentanoate hydrobromide.

Synthesis Example 3

Synthesis of Other Amino Acid Methyl Ester HBr Salts Via Chemistry Analogous to Scheme 2

Following the procedure of Synthesis Example 2 above, 2-benzyloxycarbonylamino-3-chlorocarbonylpropionic acid methyl ester is reacted with the appropriate substituted magnesium chloride starting materials in the presence of Cu$^+$ to prepare the HBr salts of the following amino acid methyl esters:

(S)-methyl 2-amino-4,4-difluoro-4-phenylbutanoate hydrobromide

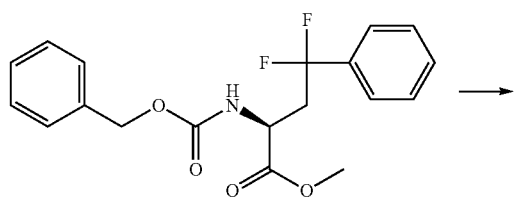

(S)-methyl 2-(benzyloxycarbonylamino)-4,4-difluoro-4-phenylbutanoate

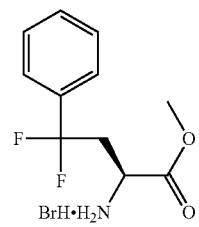

(S)-methyl 2-amino-4,4-difluoro-4-phenylbutanoate hydrobromide (S)-methyl 2-(benzyloxycarbonylamino)-4,4-difluoro-4-phenylbutanoate: $^1$H-NMR (CDCl$_3$) δ 7.2-7.4 (4H, m), 5.4 (1H), 5.05 (2H), 4.6 (1H), 3.7 (3H), 3.15 (2H), 2.3 (2H). $^{19}$F-NMR (CDCl$_3$) δ −95 ppm.

(S)-methyl 2-amino-4,4-difluoro-6-methylheptanoate hydrobromide

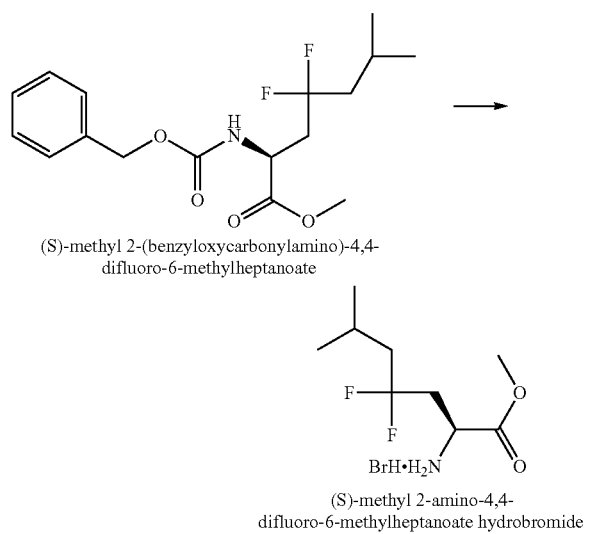

(S)-methyl 2-(benzyloxycarbonylamino)-4,4-difluoro-6-methylheptanoate: $^1$H-NMR (CDCl$_3$) δ 7.3-7.4 (5H, m), 5.55 (d), 5.2 (s), 4.6 (m), 3.8 (s), 2.3-2.5 (m), 1.65-2.0 (m). $^{19}$F-NMR (CDCl$_3$) δ −94 ppm (S)-methyl 2-amino-4,4-difluorohexanoate hydrobromide

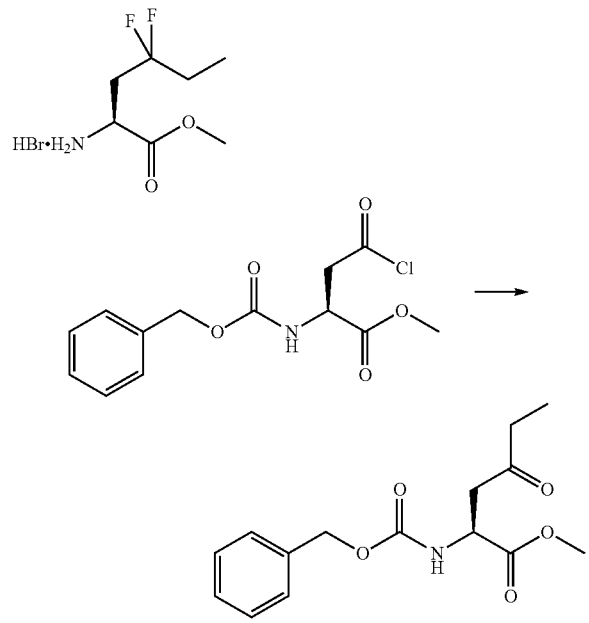

Following the procedure of Synthesis Example 2, (S)-methyl 2-(benzyloxycarbonylamino)-4-oxohexanoate was prepared from ethyl magnesium chloride (6 mL, 12 mmol), Cu$^+$ and (S)-methyl 2-(benzyloxycarbonylamino)-4-chloro-4-oxobutanoate (3 g, 10 mmol).

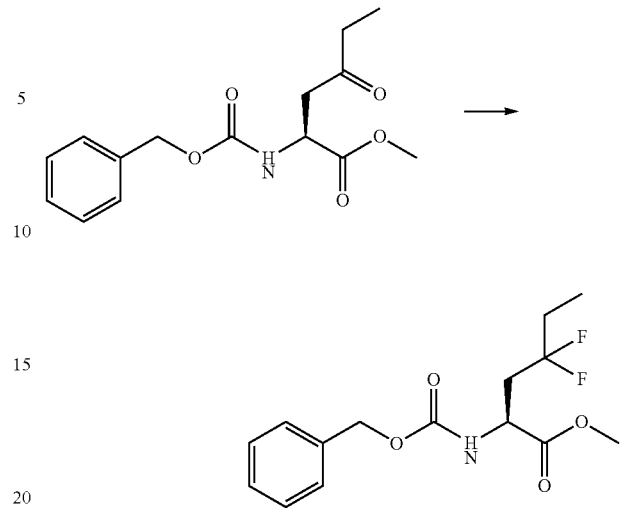

(S)-methyl 2-(benzyloxycarbonylamino)-4-oxohexanoate (0.6 g, 2.04 mmol, 1 eq.) and Deoxyfluor (50% in toluene (Agros); 2.8 g, 1.7 mmol, 5 eq.) were combined in a nalgene container and ethanol (30 µL) was added. The mixture was stirred at RT overnight, followed by heating at 35° C. for 45 min., to give (S)-methyl 2-(benzyloxycarbonylamino)-4,4-difluorohexanoate. See, *Synthesis* 2002, 17: 2561-2578. $^1$H-NMR (CDCl$_3$) δ 7.9 (1H, d), 7.2-7.4 (5H, m), 4.2-4.3 (1H, m), 5.05 (s, 214), 4.3 (1H, m), 3.65 (3H, m), 2.2-2.4 (2H, m), 1.8-2.0 (2H, m), 0.9 (3H, m); $^{19}$F-NMR (CDCl$_3$) δ −97.5 (dd) ppm

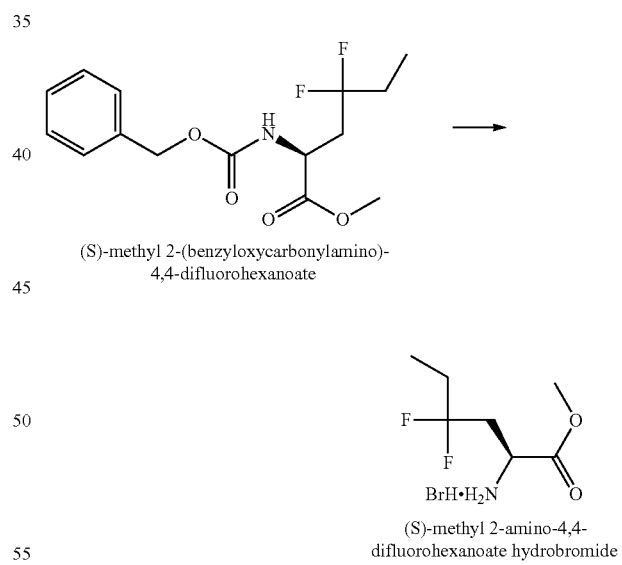

Following the procedure of Synthesis Example 2, a mixture of (S)-methyl 2-(benzyloxycarbonylamino)-4,4-difluorohexanoate and hydrogen bromide were reacted together to give (S)-methyl 2-amino-4,4-difluorohexanoate hydrobromide.

(S)-methyl 2-amino-4,4-difluorooctanoate hydrobromide: Following the procedure of Synthesis Example 2, (S)-methyl 2-(benzyloxycarbonylamino)-4-oxooctanoate was prepared from n-butyl magnesium chloride, Cu$^+$ and (S)-methyl 2-(benzyloxycarbonylamino)-4-chloro-4-oxobutanoate.

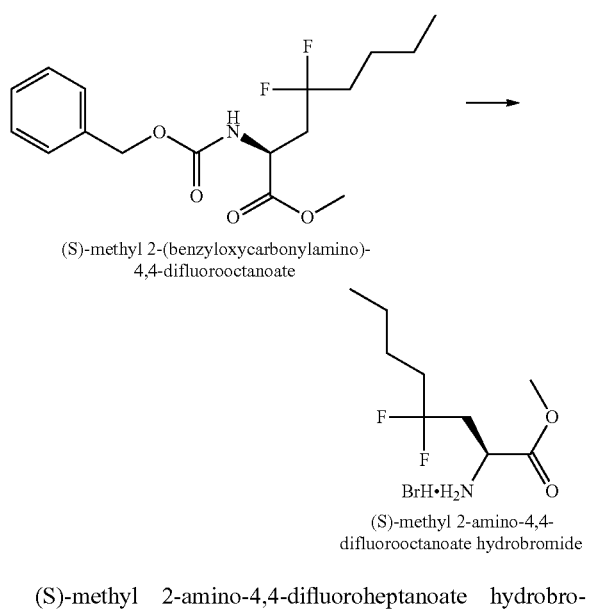

(S)-methyl 2-(benzyloxycarbonylamino)-
4,4-difluorooctanoate (S)-methyl 2-amino-4,4-
difluorooctanoate hydrobromide (S)-methyl 2-amino-4,4-difluoroheptanoate hydrobromide: Following the procedure of Synthesis Example 2, (S)-methyl 2-(benzyloxycarbonylamino)-4-heptanoate was prepared from n-butyl magnesium chloride, Cu⁺ and (S)-methyl 2-(benzyloxycarbonylamino)-4-chloro-4-oxobutanoate.

(S)-methyl 2-(bezyloxycarbonylamino)-
4,4-difluoroheptanoate (S)-methyl 2-amino-4,4-
difluoroheptanoate hydrobromide (S)-methyl 2-(benzyloxycarbonylamino)-4,4-difluoroheptanoate: $^1$H-NMR (CDCl$_3$) δ 7.9 (d), 7.2-7.4 (5H, m), 5.0 (3H, s), 4.3 (1H, m), 3.6 (s, 3H), 2.2-2.5 (m), 1.7-1.9 (m), 1.4-1.9 (m), 0.7-0.9 (m); $^{19}$F-NMR (CDCl$_3$) δ −95 ppm.

(S)-methyl
2-amino-4-cyclopentyl-4,4-difluorobutanoate

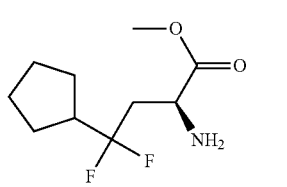

(S)-methyl
2-amino-4-cyclohexyl-4,4-difluorobutanoate

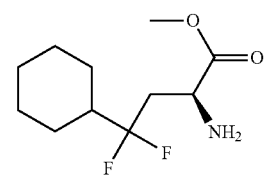 [SMILES: COC(=O)[C@@H](N)CC(F)(F)C1CCCCC1]

Synthesis Example 4

Scheme 3

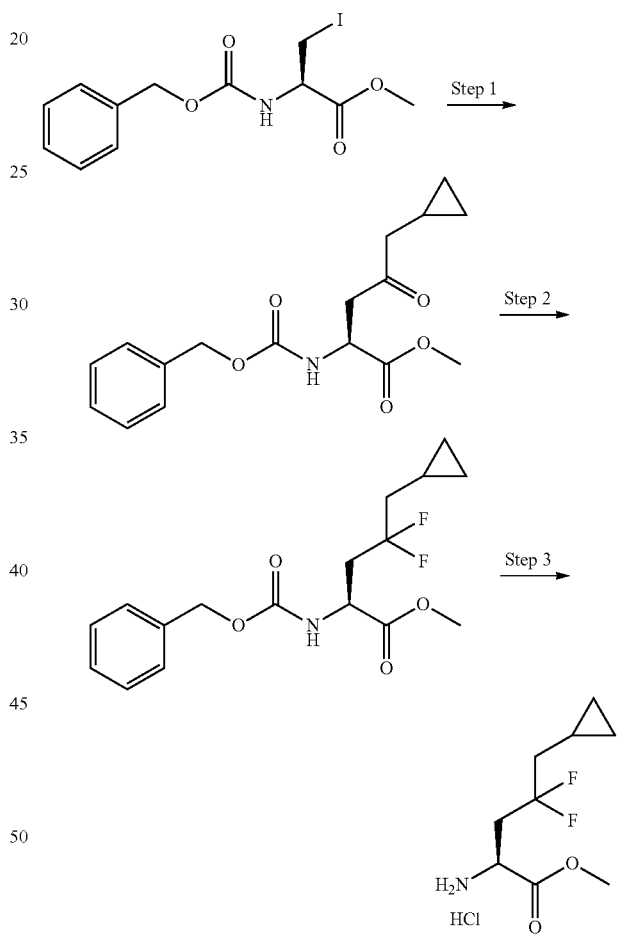

Scheme 3, Step 1: (S)-methyl 2-(benzyloxycarbonylamino)-5-cyclopropyl-4-oxopentanoate

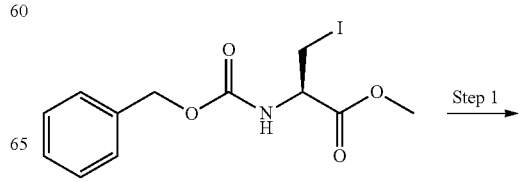

-continued

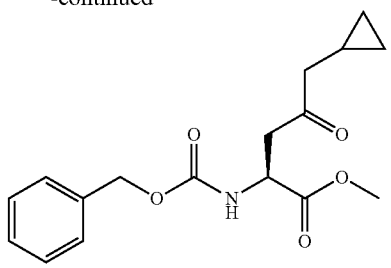

Zinc dust (785 mg, 12 mmol) was heated under vacuum for 5 min. and then allowed to cool to RT. The flask was purged with dry $N_2$ (2×). Dry phenol (12 mL) and dry DMA (0.8 mL) were added to the flask and the mixture was warmed to about 50° C. with vigorous stirring. 1,2-Dibromoethane (14 µL) was added and the mixture was then allowed to cool to RT and stirred for 30 min., after which TMSCl was added. The mixture was stirred at RT for another 30 min, after which R-benzyloxycarbonylamino-3-iodopropionic acid methyl ester (981 mg, 3 mmol) was added. After about 90 min., palladium catalyst (such as $PdCl_2(PPh_3)_2$) and cyclopropylmethylcarbonyl chloride (3 mmol) were added and the reaction was stirred for another 45 min., to give 520 mg of (S)-methyl 2-(benzyloxycarbonylamino)-5-cyclopropyl-4-oxopentanoate. $^1$H-NMR (500 MHz, $CDCl_3$): 7.36 (5H, m, Ar—H), 5.79 (1H, bs, NH), 5.14 (2H, S, 2H), 4.59 (1H, m, NCH), 3.78 (3H, s, OMe), 3.18 (2H, dd, $CH_2$), 2.29 (2H, m, $CH_2$), 0.92 (1H, m, CH), 0.59 (2H, m, $CH_2$), 0.16 (2H, m, $CH_2$). EIMS (m/z): 320.14 (M$^+$+1)

Scheme 3, Step 2: (S)-methyl 2-(benzyloxycarbonylamino)-5-cyclopropyl-4,4-difluoropentanoate

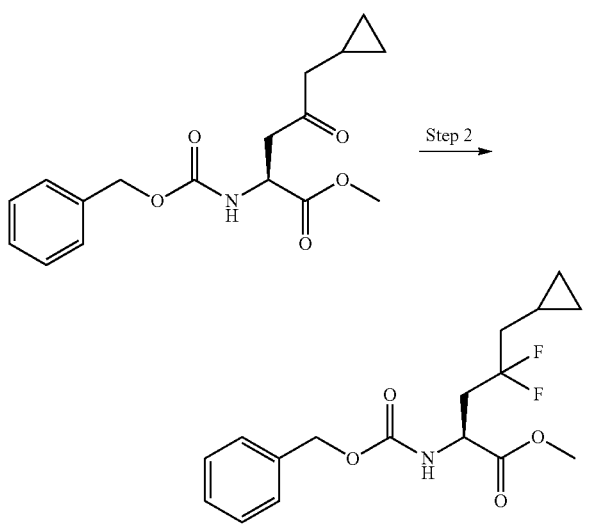

A mixture of (S)-methyl 2-(benzyloxycarbonylamino)-5-cyclopropyl-4-oxopentanoate (285 mg, 1 mmol) and DAST (0.92 mL, 5 mmol) was stirred at RT in a sealed tube for 48 hr. The mixture was then diluted with methylene chloride and quenched with sat. $NaHCO_3$ (9.2 µL), after which it was partitioned between $CH_2Cl_2$ and sat. $NaHCO_3$. The $CH_2Cl_2$ extracts were dried and concentrated in vacuo, and the residue was purified by flash chromatography (1:4-hexane:ethanol) to give 100 mg of (S)-methyl 2-(benzyloxycarbonylamino)-5-cyclopropyl-4,4-difluoropentanoate as a colorless oil. $^1$H-NMR (500 MHz, $CDCl_3$): 7.38 (5H, m, Ar—H), 5.49 (1H, bs, NH), 5.18 (2H, S, 2H), 4.61 (1H, m, NCH), 3.78 (3H, s, OMe), 2.52 (2H, m, $CH_2$), 1.80 (2H, m, $CH_2$), 0.82 (1H, m, CH), 0.59 (2H, m, $CH_2$), 0.16 (2H, m, $CH_2$). EIMS (m/z): 342.12 (M$^+$+1).

Scheme 3, Step 3: (S)-Methyl 2-amino-5-cyclopropyl-4,4-difluoropentanoate hydrochloride

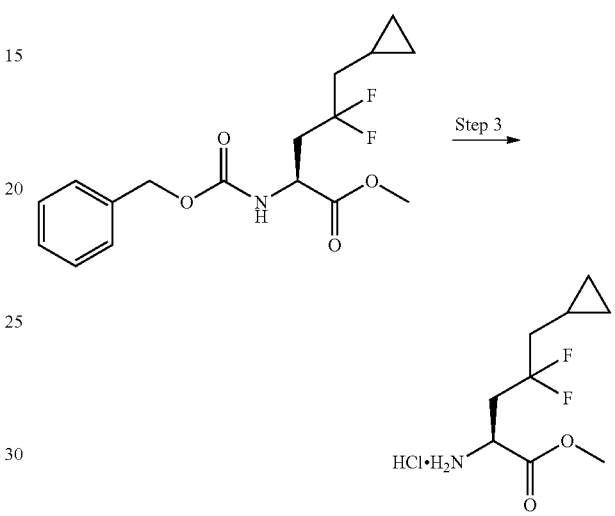

A solution of (S)-methyl 2-(benzyloxycarbonylamino)-5-cyclopropyl-4,4-difluoropentanoate (570 mg, 1.87 mmol) in dioxane/4N-HCl (9 mL, 37 mmol) was stirred at RT for two hr, after which the solvent was removed by rotoevaporation to give 450 mg of (S)-methyl 2-amino-5-cyclopropyl-4,4-difluoropentanoate hydrochloride as a beige solid.

Synthesis Example 4

Scheme 4

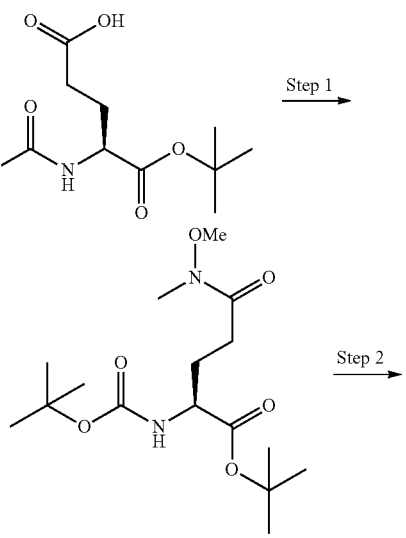

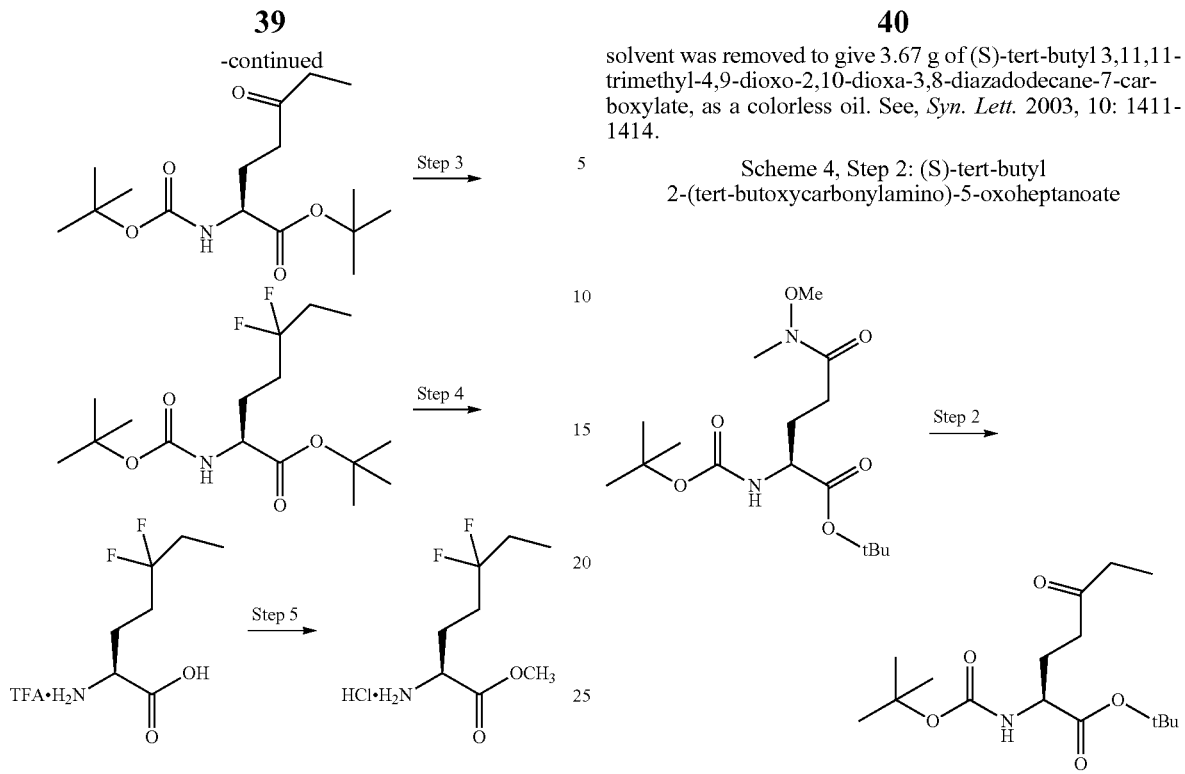

Scheme 4, Step 1: (S)-methyl 2-(boc-amino)-5-chloro-5-oxopentanoate (S)-5-tert-butoxy-4-(tert-butoxycarbonylamino)-5-oxopentanoic acid (S)-tert-butyl 3,11,11-trimethyl-4,9-dioxo-2,10-dioxa-3,8-diazadodecane-7-carboxylate A mixture of (S)-5-tert-butoxy-4-(tert-butoxycarbonylamino)-5-oxopentanoic acid (3.03 g, 10 mmol) and methoxymethylamine HCl (1.17 g, 12 mmol) in HOBt (1.62 g, 12 mmol), EDC (2.3 g, 12 mmol) and NMM (3.3 mL, 30 mmol) was stirred at RT for 2 hr. The reaction was washed with 1N-HCl, NaHCO$_3$ and sat. NaCl and dried over MgSO$_4$. The solvent was removed to give 3.67 g of (S)-tert-butyl 3,11,11-trimethyl-4,9-dioxo-2,10-dioxa-3,8-diazadodecane-7-carboxylate, as a colorless oil. See, *Syn. Lett.* 2003, 10: 1411-1414.

Scheme 4, Step 2: (S)-tert-butyl 2-(tert-butoxycarbonylamino)-5-oxoheptanoate

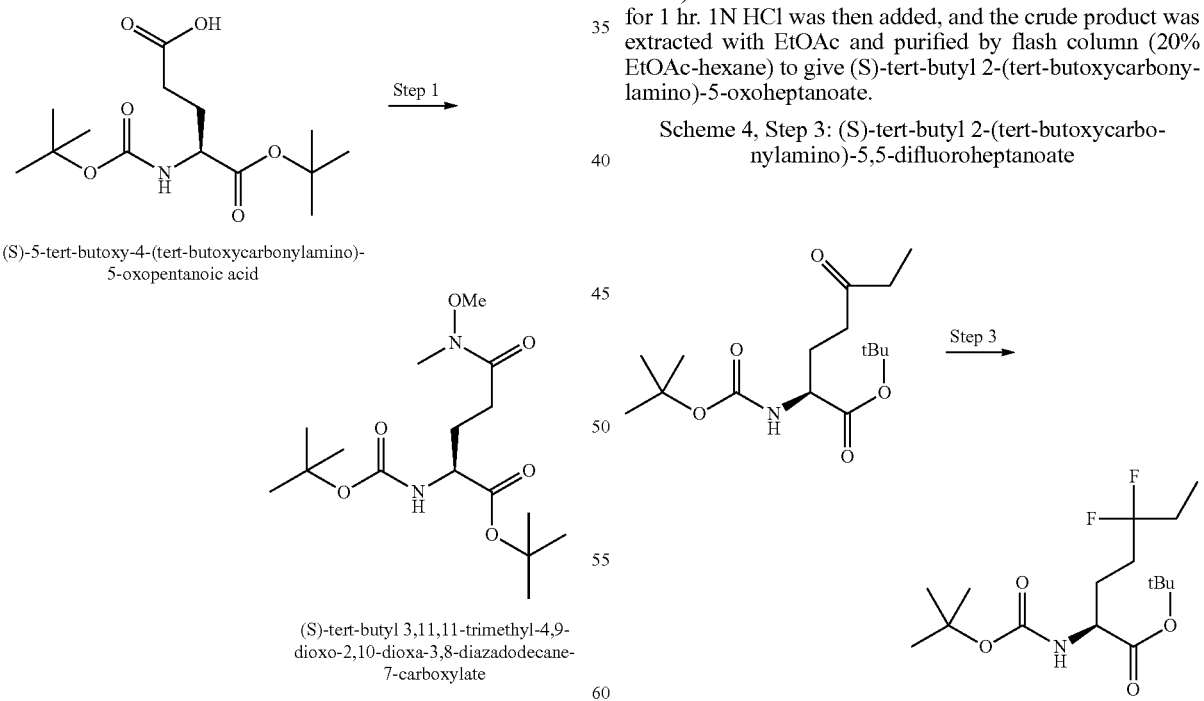

The above butanoic acid ester ((S)-tert-butyl 3,11,11-trimethyl-4,9-dioxo-2,10-dioxa-3,8-diazadodecane-7-carboxylate) (1.38 g, 4 mmol) was dissolved in THF and cooled to −40° C., after which ethyl magnesium chloride (5 mL, 10 mmol) was added. The reaction mixture was stirred at −40° C. for 1 hr. 1N HCl was then added, and the crude product was extracted with EtOAc and purified by flash column (20% EtOAc-hexane) to give (S)-tert-butyl 2-(tert-butoxycarbonylamino)-5-oxoheptanoate.

Scheme 4, Step 3: (S)-tert-butyl 2-(tert-butoxycarbonylamino)-5,5-difluoroheptanoate Following the procedure of Synthesis Example 2, Scheme 2, Step 3, (S)-tert-butyl 2-(tert-butoxycarbonylamino)-5-oxoheptanoate (1 g) and Deoxyfluor (5 mL) were reacted together in the presence of catalytic amount of ethanol to give (S)-tert-butyl 2-(tert-butoxycarbonylamino)-5,5-difluoroheptanoate.

Scheme 4, Step 4: (S)-methyl
2-amino-5,5-difluoroheptanoate TFA salt

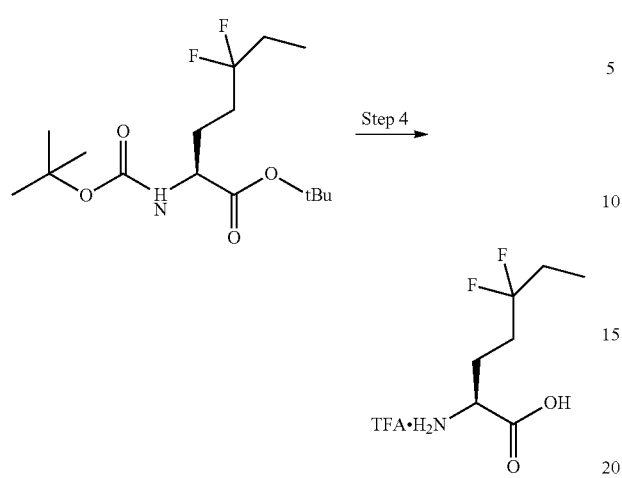

(S)-tert-butyl 2-(tert-butoxycarbonylamino)-5,5-difluoro-heptanoate (1 mmol) and TFA (5 mL) were stirred together at RT for 1 hr. The solvent was then removed and diethyl ether was added to precipitate out the solid, which was then filtered to give (S)-methyl 2-amino-5,5-difluoroheptanoate TFA salt.

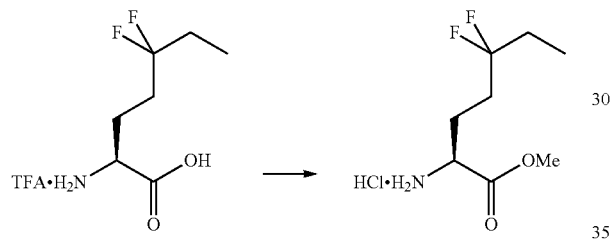

The (S)-methyl 2-amino-5,5-difluoroheptanoate TFA salt (1 mmol) was dissolved in methanol (5 mL) and benzene (5 mL), after which TMS-diazomethane (2.0M in hexane; 3 mL) was added and the mixture stirred at RT for 10 min. The solvent was removed and HCl in dioxane was added, after which solvent was again removed. Diethyl ether was added to precipitate out the solid, which was then filtered to give (S)-methyl 2-amino-5,5-difluoroheptanoate hydrochloride.

Synthesis Example 5

Synthesis of Other Amino Acid Methyl Esters

Following the procedure of Synthesis Example 4, Scheme 4 above, the following amino acid methyl esters are prepared from the appropriate starting materials:

(S)-methyl
2-amino-5-cyclopropyl-5,5-difluoropentanoate

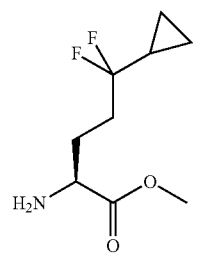

(S)-methyl 2-amino-5,5-difluoro-5-phenylpentanoate (S)-methyl 2-amino-5,5-difluoro-6-phenylhexanoate

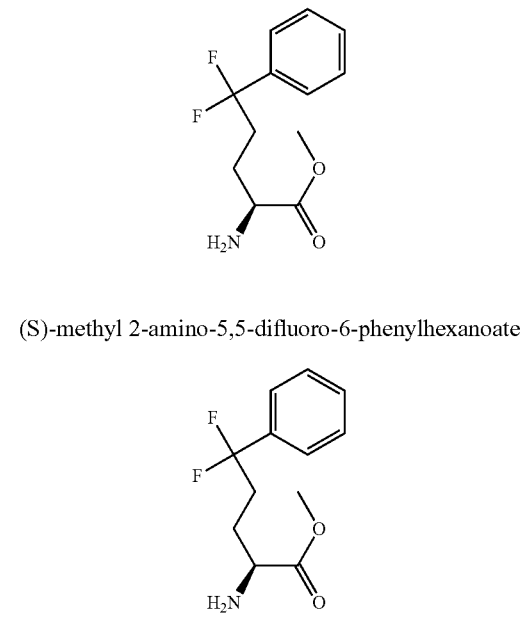

Synthesis Example 6

Scheme 5

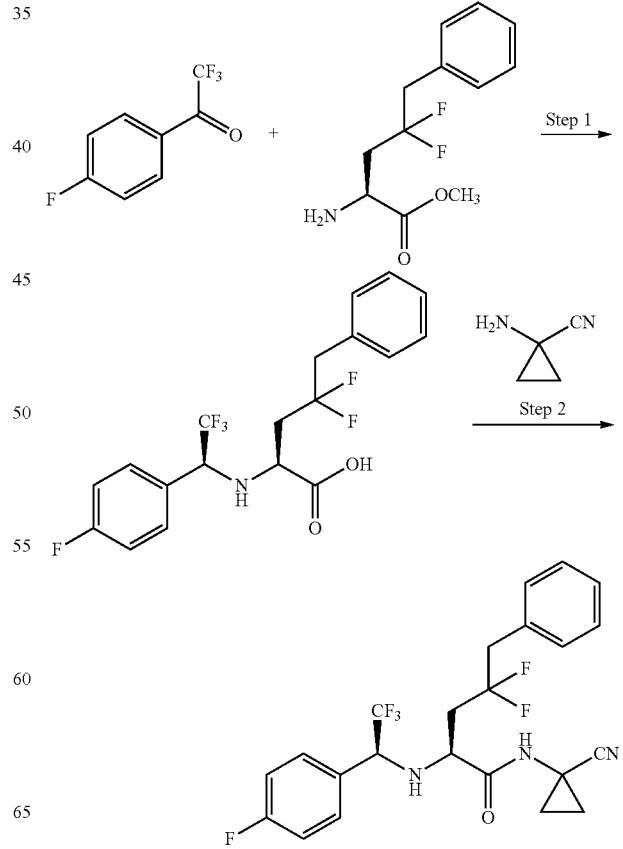

Scheme 5, Step 1: (S)-4,4-difluoro-5-phenyl-2-((S)-2,2,2-trifluoro-1-(4-fluorophenyl)ethylamino)pentanoic acid

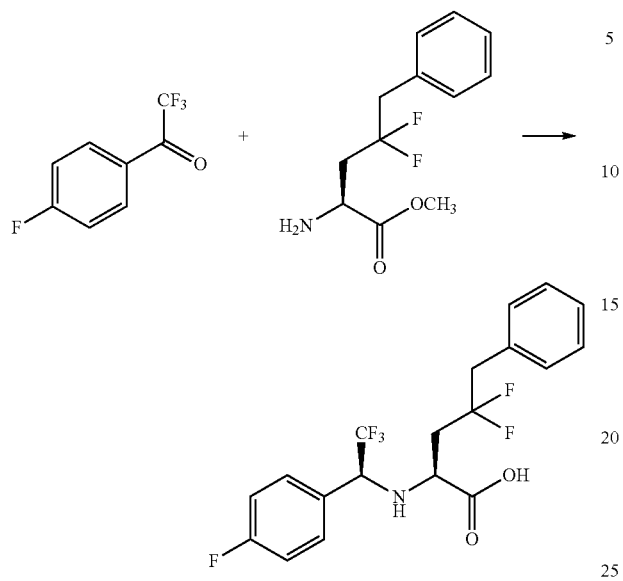

Methyl (S)-methyl 2-amino-4,4-difluoro-5-phenylpentanoate HBr salt (2.44 mmol, 1 eq.) was dissolved in dry methanol. Trifluoromethyl 4-fluorophenyl ketone (2.44 mmol, 1 eq.) and potassium carbonate (4.88 mmol, 2 eq.) were added, and the mixture was heated at 50° C. overnight. To the resulting condensation (imine-formation) reaction product was added, at −30° C., a suspension of $Zn(BH_4)_2$ (ca. 1.1 eq.) [which was prepared from $NaBH_4$ (1 eq.) and $ZnCl_2$ (1M in diethyl ether; 2 eq.)], and the mixture was allowed to warm to RT overnight. The reaction was quenched with 1 N HCl and extracts with ethyl acetate, dried and concentrated to give the crude product, (S)-4,4-difluoro-5-phenyl-2-((S)-2,2,2-trifluoro-1-(4-fluorophenyl)ethylamino)pentanoic acid Scheme 5, Step 2: (S)—N-(1-cyanocyclopropyl)-4,4-difluoro-5-phenyl-2-((S)-2,2,2-trifluoro-1-(4-fluorophenyl)ethylamino)pentanamide

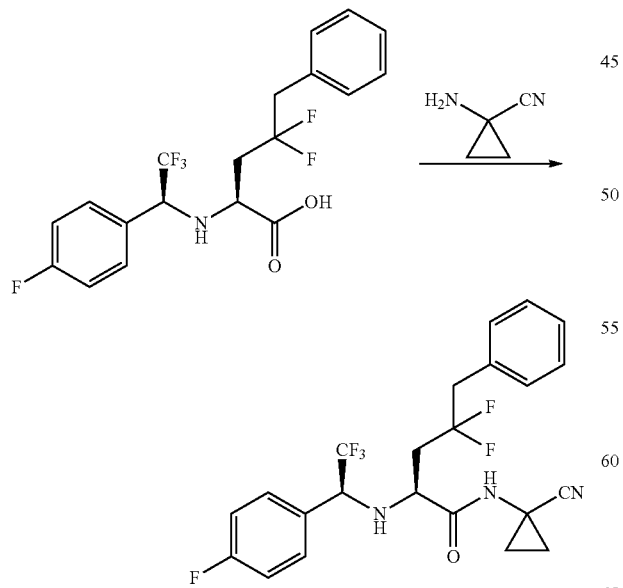

A mixture of the above pentanoic acid (S)-4,4-difluoro-5-phenyl-2-((S)-2,2,2-trifluoro-1-(4-fluorophenyl)ethylamino)pentanoic acid, (1 mmol), 1-aminocyclopropanecarbonitrile hydrochloride (1.2 mmol), HATU (1.2 mmol) and NMM (4.0 mmol), in DMF, was stirred at RT for 2 hr. Saturated ammonium chloride and ethyl acetate were then added, and the reaction was stirred an additional 20 min at RT, after which product was extracted with ethyl acetate, purified with flash column (30-35% ethyl acetate-hexane), and crystallized with DCM-hexane to give (S)—N-(1-cyanocyclopropyl)-4,4-difluoro-5-phenyl-2-((S)-2,2,2-trifluoro-1-(4-fluorophenyl)ethylamino)pentanamide as a white crystal. $^1$H-NMR (CDCl$_3$) δ 8.9 (1H), 7.2-7.5 (9H, m), 4.33 (1H, m), 3.2-3.5 (3H), 2.0-2.6 (2H), 1.6-1.8 (2H), 0.75 (1H), 0.58 (1H). $^{19}$F-NMR (CDCl$_3$) δ −113 ppm. LC/EIMS (m/z): 470 (M+Na)+.

Synthesis Example 7

Synthesis of Acid Amides of the Invention

In like manner as in Synthesis Example 6, the following amides are prepared from reaction of 1-aminocyclopropanecarbonitrile hydrochloride with the appropriate carboxylic acid derived from the corresponding difluoroamino acid ester:

(S)—N-(1-cyanocyclopropyl)-4,4-difluoro-4-phenyl-2-((S)-2,2,2-trifluoro-1-(4-fluorophenyl)ethylamino)butanamide

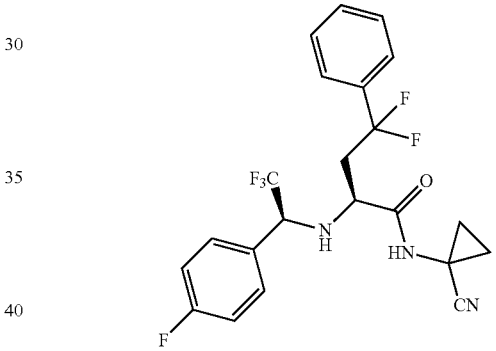

(S)—N-(1-cyanocyclopropyl)-4,4-difluoro-6-methyl-2-((S)-2,2,2-trifluoro-1-(4-fluorophenyl)ethylamino)heptanamide

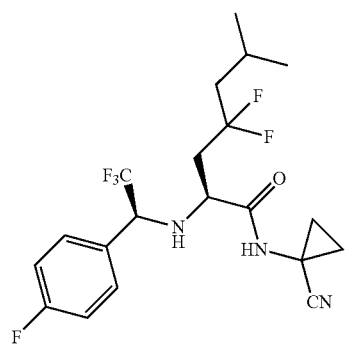 [SMILES: CC(C)CC(F)(F)C[C@H](N[C@@H](c1ccc(F)cc1)C(F)(F)F)C(=O)NC1(C#N)CC1]

$^1$H-NMR (CDCl$_3$) δ 7.4 (2H, m), 7.38-7.42 (2H, m), 6.9 (1H, s), 4.2-4.3 (1H, m), 3.2-3.55 (m), 1.9-2.5 (m), 1.75-1.9 (m), 0.9-1.1 (m). $^{19}$F-NMR (CDCl$_3$) δ −74.5 (s), −94, −112 (s) ppm. LC/EIMS (m/z): 436 (M+H)$^+$

45

(S)—N-(1-cyanocyclopropyl)-5-cyclopropyl-4,4-difluoro-2-((S)-2,2,2-trifluoro-1-(4-fluorophenyl)ethylamino)pentanamide

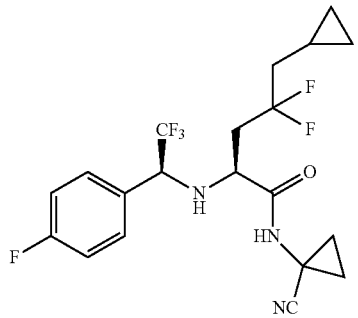 [SMILES: N#CC1(NC(=O)[C@H](CC(F)(F)CC2CC2)N[C@@H](c2ccc(F)cc2)C(F)(F)F)CC1]

¹H-NMR (CDCl₃) δ 7.45 (1H, s), 7.30-7.35 (2H, m), 7.05-7.15 (2H, m), 4.2-4.3 (1H, m), 3.4-3.5 (1H, m), 2.2-2.6 (3H, m), 1.7-1.9 (2H, m), 1.5-1.6 (m), 1.0-1.3 (2H, m), 0.7-0.9 (1H, m), 0.5-0.6 (2H, m), 0.1-0.2 (2H, m) ¹⁹F-NMR (CDCl₃) δ −74.8 (s), −95.4, −111.5 (s) ppm. LC/EIMS (m/z): 434 (M+H)⁺

(S)—N-(1-cyanocyclopropyl)-4,4-difluoro-2-((S)-2,2,2-trifluoro-1-(4-fluorophenyl)ethylamino)hexanamide

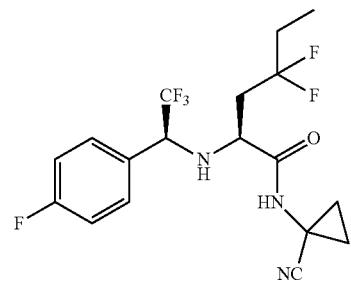 [SMILES: CCC(F)(F)C[C@H](N[C@@H](c1ccc(F)cc1)C(F)(F)F)C(=O)NC1(C#N)CC1]

¹H-NMR (CDCl₃) δ 7.5 (1H, s), 7.38-7.42 (2H, m), 7.1-7.2 (2H, m), 4.2-4.3 (1H, m), 3.45-3.50 (1H, m), 2.2-2.5 (m), 1.8-2.0 (m), 1.0-1.2 (m) ¹⁹F-NMR (CDCl₃) δ −74.5 (s), −98.5 (dd), −111 (s) ppm. LC/EIMS (m/z): 408 (M+H)⁺

(S)—N-(1-cyanocyclopropyl)-4,4-difluoro-2-((S)-2,2,2-trifluoro-1-(4-fluorophenyl)ethylamino)heptanamide

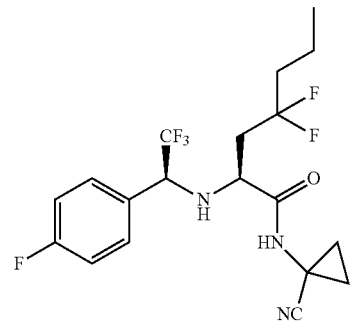 [SMILES: CCCC(F)(F)C[C@H](N[C@@H](c1ccc(F)cc1)C(F)(F)F)C(=O)NC1(C#N)CC1]

46

¹H-NMR (d₆-DMSO) δ 8.9 (s), 7.2-7.5 (m), 7.2-7.3 (m), 4.3-4.4 (1H, m), 3.2-3.5 (m), 2.0-2.3 (2H, m), 1.3-1.4 (m), 0.9-0.8 (1H, m), 0.4-0.5 (1H, m); ¹⁹F-NMR (CDCl₃) δ −73.1 (s), −98.0, −113.2 (s) ppm. LC/EIMS (m/z): 421.9 (M+H)⁺

(S)—N-(1-cyanocyclopropyl)-4,4-difluoro-2-((S)-2,2,2-trifluoro-1-(4-fluorophenyl)ethylamino)octanamide

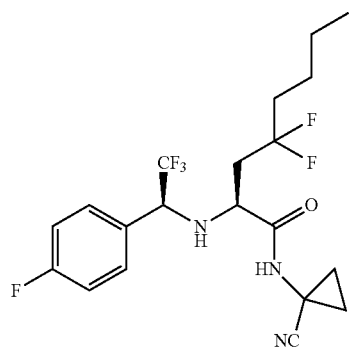 [SMILES: CCCCC(F)(F)C[C@H](N[C@@H](c1ccc(F)cc1)C(F)(F)F)C(=O)NC1(C#N)CC1]

(S)—N-(1-cyanocyclopropyl)-4-cyclopropyl-4,4-difluoro-2-((S)-2,2,2-trifluoro-1-(4-fluorophenyl)ethylamino)butanamide

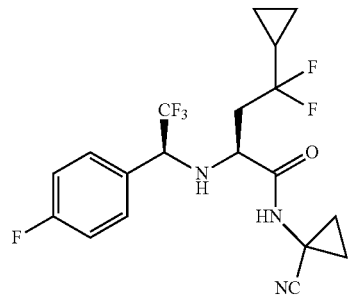 [SMILES: N#CC1(NC(=O)[C@H](CC(F)(F)C2CC2)N[C@@H](c2ccc(F)cc2)C(F)(F)F)CC1]

(S)—N-(1-cyanocyclopropyl)-4-cyclohexyl-4,4-difluoro-2-((S)-2,2,2-trifluoro-1-(4-fluorophenyl)ethylamino)butanamide

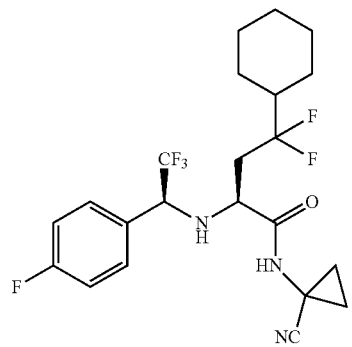 [SMILES: N#CC1(NC(=O)[C@H](CC(F)(F)C2CCCCC2)N[C@@H](c2ccc(F)cc2)C(F)(F)F)CC1]

47

(S)—N-(1-cyanocyclopropyl)-5,5-difluoro-2-((S)-2,2,2-trifluoro-1-(4-fluorophenyl)ethylamino)heptanamide

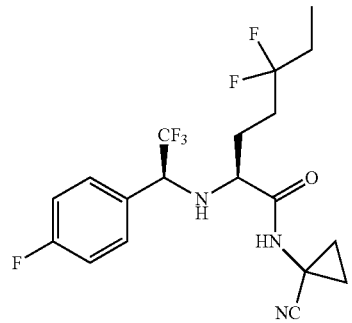 [SMILES: CCC(F)(F)CC[C@H](N[C@@H](c1ccc(F)cc1)C(F)(F)F)C(=O)NC1(C#N)CC1]

$^1$H-NMR (d$_6$-DMSO) δ 8.9 (s), 7.2-7.5 (m), 7.2-7.3 (m), 4.3-4.4 (1H, m), 3.2-3.5 (m), 2.0-2.3 (2H, m), 1.3-1.4 (m), 0.9-0.8 (1H, m), 0.4-0.5 (1H, m); $^{19}$F-NMR (CDCl$_3$) δ −73.1 (s), −98.0, −113.2 (s) ppm. LC/EIMS (m/z): 421 (M+H)$^+$ Rt=6.01 min.

(S)—N-(1-cyanocyclopropyl)-5-cyclopropyl-5,5-difluoro-2-((S)-2,2,2-trifluoro-1-(4-fluorophenyl)ethylamino)pentanamide

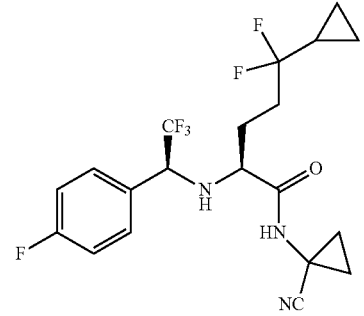 [SMILES: N#CC1(NC(=O)[C@H](CCC(F)(F)C2CC2)N[C@@H](c2ccc(F)cc2)C(F)(F)F)CC1]

(S)—N-(1-cyanocyclopropyl)-5,5-difluoro-5-phenyl-2-((S)-2,2,2-trifluoro-1-(4-fluorophenyl)ethylamino)pentanamide

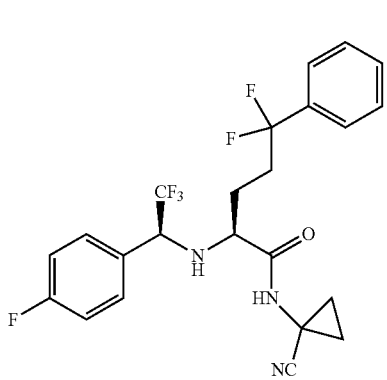 [SMILES: N#CC1(NC(=O)[C@H](CCC(F)(F)c2ccccc2)N[C@@H](c2ccc(F)cc2)C(F)(F)F)CC1]

48

(S)—N-(1-cyanocyclopropyl)-5,5-difluoro-6-phenyl-2-((S)-2,2,2-trifluoro-1-(4-fluorophenyl)ethylamino)hexanamide

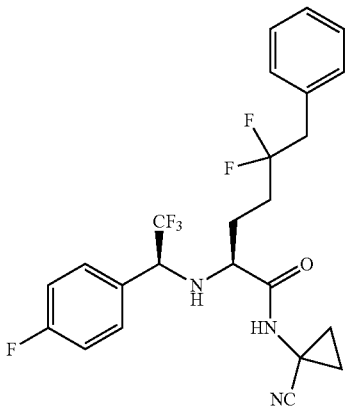 [SMILES: N#CC1(NC(=O)[C@H](CCC(F)(F)Cc2ccccc2)N[C@@H](c2ccc(F)cc2)C(F)(F)F)CC1]

Synthesis Example 8

Scheme 6

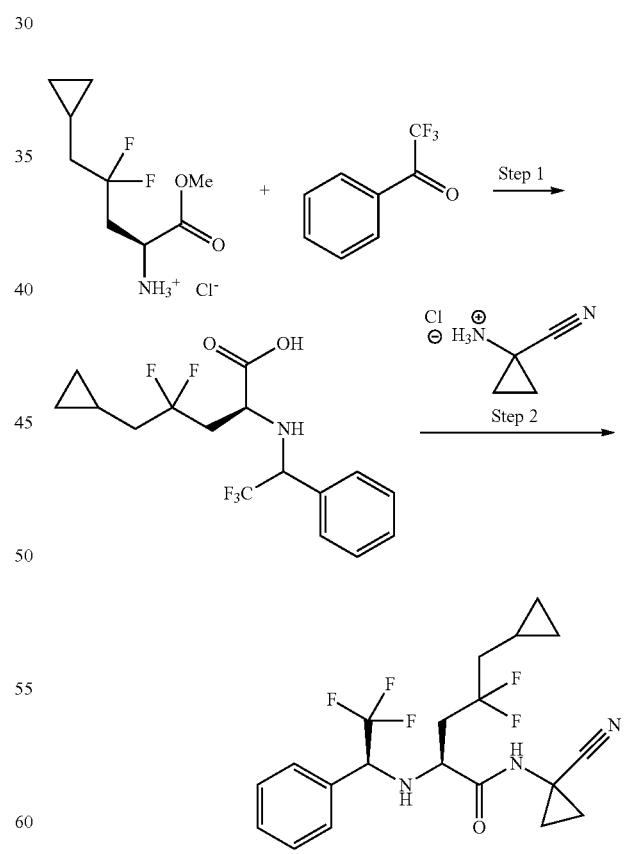

In a manner analogous to the chemistry described in Synthesis Example 6, Scheme additional analogs were synthesized by varying the substitution on the phenyl ring of 2,2,2-trifluoro-1-phenylethanone.

Scheme 6, Step 1: (S)-5-cyclopropyl-4,4-difluoro-2-((S)-2,2,2-trifluoro-1-phenylethylamino)pentanoic acid

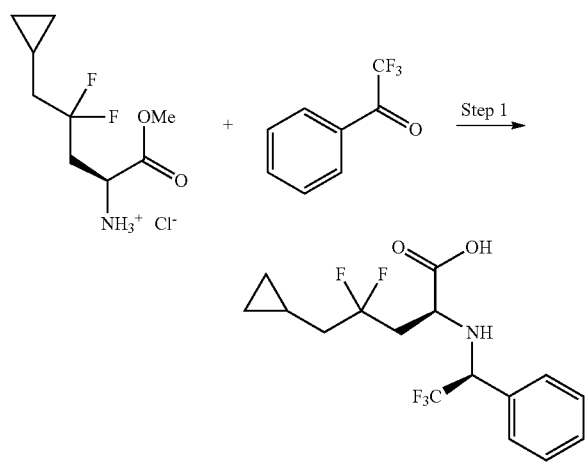

(S)-5-cyclopropyl-4,4-difluoro-1-methoxy-1-oxopentan-2-amine hydrochloride (250 mg, 10 mmol), trifluoroacetophenone (179 mg, 10 mmol), potassium carbonate (426 mg, 30 mmol) was charged in isopropanol (10 mL) under nitrogen. The reaction mixture stirred for 20 h at 60° C. When TLC showed an absence of starting material, is the mixture was filtered under hot and the solids were washed with isopropanol (20 mL) and the filtrates were combined and concentrated under reduced pressure. The residue (400 mg, 10 mmol) was dissolved in acetonitrile (5 mL) and methanol (1 mL) and transferred to a dropping funnel under nitrogen. The zinc borohydride suspension prepared as described above was cooled to −45° C. and treated with the imine solution which was added drop-wise and the reaction was stirred at same temperature for 1 h. Once the staring material was consumed, is the reaction mixture was quenched with 1N HCl solution (10 mL) at 0° C. and then allowed to warm to room temperature. The mixture was extracted with ethyl acetate (3×40 mL) and the combined organic extracts washed with water (50 mL) and brine (50 mL). The organic extracts were evaporated under reduced pressure, and the residue re-dissolved in ethyl acetate (20 mL) and washed with water (20 mL) and brine (50 mL). The solution was dried (MgSO$_4$) and the solvent evaporated under reduced pressure to give (S)-5-cyclopropyl-4,4-difluoro-2-((S)-2,2,2-trifluoro-1-phenylethylamino)pentanoic acid as a pale oil (265 mg, 71.3%).

Preparation of Zinc Borohydride: Zinc chloride (1.0 g, 7.3 mmol) was suspended in 1,2-DME (10 mL) under nitrogen and stirred for 1 h at room temperature. The resulting white slurry was cooled to ~5° C. and treated in portions with sodium borohydride (550 mg, 14 mmol). The ice bath was removed and the mixture was stirred at room temperature for 24 h to give a light grey suspension of Zn(BH$_4$)$_2$.

Scheme 6, Step 2: (S)—N-(1-cyanocyclopropyl)-5-cyclopropyl-4,4-difluoro-2-((S)-2,2,2-trifluoro-1-phenylethylamino)pentanamide

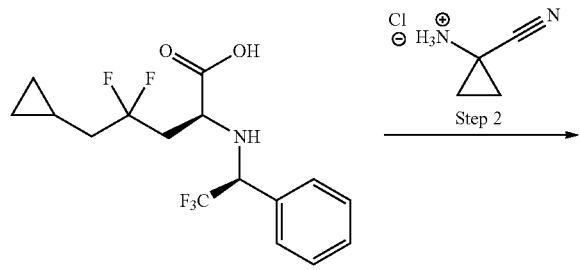

-continued

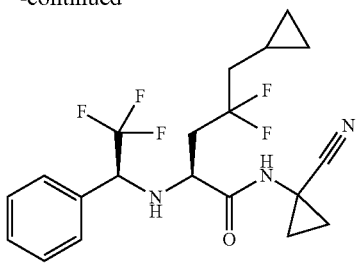

A stirred solution of (S)-5-cyclopropyl-4,4-difluoro-2-((S)-2,2,2-trifluoro-1-phenylethylamino)pentanoic acid (150 mg, 0.4 mmol) in DMF (15 mL) was treated with HATU (253 mg, 0.5 mmol) and DIPEA (0.3 mL, 1.7 mL mmol). After 15 min, 1-cyanocyclopropane hydrochloride (61 mg, 0.5 mmol) was added and the reaction mixture was stirred under a nitrogen atmosphere for 2 h. Once the reaction was complete, the reaction mixture was quenched with saturated sodium bicarbonate solution, extracted with ethyl acetate & washed with 1HCl solution and brine, dried over Na$_2$SO$_4$, filtered and was concentrated. The crude compound was purified by silica gel column chromatography eluting with 10% ethyl acetate in hexane followed by re-crystallization from DCM and pentane to provide (S)—N-(1-cyanocyclopropyl)-5-cyclopropyl-4,4-difluoro-2-((S)-2,2,2-trifluoro-1-phenylethylamino)pentanamide (65 mg, 37%) as white solid. $^1$H-NMR (500 MHz, DMSO-d$_6$): 8.88 (1H, s, NH), 7.38 (5H, s, Ar—H), 4.23 (1H, m, CHCF$_3$), 3.39 (1H, m, CH), 3.18 (1H, m, NH), 2.23 (2H, m, CH$_2$), 1.94 (2H, m, CH$_2$), 1.32 (2H, m, CH$_2$), 0.82 (2H, m, CH$_2$), 0.57 (1H, m, CH), 0.45 (2H, m, CH$_2$), 0.12 (2H, m, CH$_2$). $^{19}$F-NMR (500 MHz, CD$_3$OD): −74.609 (CF$_2$), −95.308, −95.507 (CF$_3$). EIMS (m/z): 416 (M+H)$^1$. HPLC: 97.37% (RT 16.39) Column used zorbax SB, C8, 250×4.6 mm, 5 uMobile Phase: ACN (B): 0.1% TFA in water (A) Flow rate: 1.0 mL/Min

Synthesis Example 9

Synthesis of Acid Amides of the Invention

In like manner as in Synthesis Example 8, the following amides are prepared from reaction of 1-aminocyclopropanecarbonitrile hydrochloride with the appropriate carboxylic acid derived from the corresponding difluoroamino acid ester:

(S)—N-(1-cyanocyclopropyl)-5-cyclopropyl-4,4-difluoro-2-((S)-2,2,2-trifluoro-1-(4-methoxyphenyl)ethylamino)pentanamide

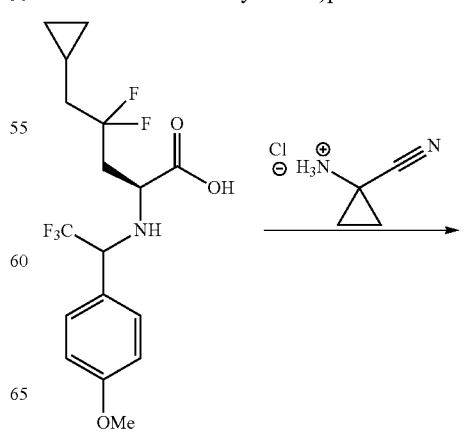

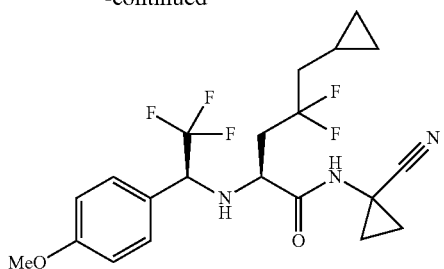

$^1$H-NMR (500 MHz, CD$_3$OD): 7.28, 6.93 (4H, A$_2$B$_2$, Ar—H), 4.18 (1H, m, CHCF$_3$), 3.79 (3H, s, OMe), 3.42 (1H, m, CH), 2.33 (2H, m, CH$_2$), 1.84 (2H, m, CH$_2$), 1.38 (2H, m, CH$_2$), 1.01 (1H, m, CH), 0.82 (2H, m, CH$_2$), 0.53 (2H, m, CH$_2$), 0.19 (2H, m, CH$_2$). $^{13}$C-NMR (500 MHz, CD$_3$OD): 176.90 (1C, CO), 161.85 (1C, ArC-OMe), 130.95 (2C, ArC), 127.64 (1C, ArC), 125.78 (1C, CF$_3$), 120.97 (1C, CN), 115.17 (2C, ArC), 97.26 (2C, CF$_2$), 64.17 (1C, q, CCF$_3$), 57.49 (1C, OCH$_3$), 55.79 (1C, CHN), 42.81 (1C, t, CCF$_2$), 40.50 (1C, t, CCF$_2$), 21.02 (1C, C), 16.83, 16.65 (2C, CH$_2$), 5.53 (1C, CCH), 4.60, 4.52 (2C, CH$_2$) $^{19}$F-NMR (500 MHz, CD$_3$OD): −74.609, −74.940 (CF$_2$), −95.308, −95.606 (CF$_3$). EIMS (m/z): 446 (M+H)$^1$. HPLC: 98.95% (RT 16.41) Column used zorbax SB, C8, 250×4.6 mm, 5 u. Mobile Phase: ACN (A): 0.1% TFA in water (B). Flow rate: 1.5 mL/Min (S)—N-(1-cyanocyclopropyl)-5-cyclopropyl-2-((S)-1-(3,4-difluorophenyl)-2,2,2-trifluoroethylamino)-4,4-difluoropentanamide

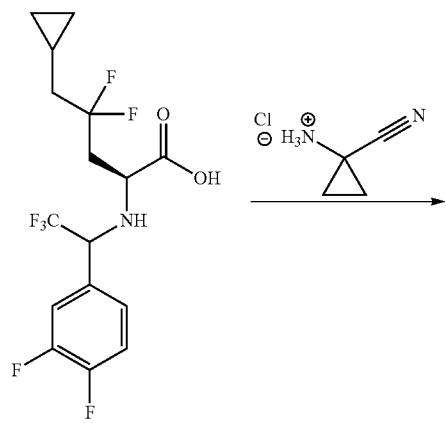

$^1$H-NMR (500 MHz, CD$_3$OD): 7.42-7.21 (3H, m, Ar—H), 4.25 (1H, m, CHCF$_3$), 3.42 (1H, m, CH), 2.37 (2H, m, CH$_2$), 1.83 (2H, m, CH$_2$), 1.41 (2H, m, CH$_2$), 0.99 (2H, m, CH$_2$), 0.82 (1H, m, CH), 0.57 (2H, m, CH$_2$), 0.19 (2H, m, CH$_2$). $^{19}$F-NMR (500 MHz, CD$_3$OD): −74.808 (CF$_2$), −95.308, −95.705 (CF$_3$), −135.646, −135.844 (2×Ar—F). EIMS (m/z): 452 (M+H)$^1$. HPLC: 94.12% (RT 16.70) Column used zorbax SB, C8, 250×4.6 mm, 5 u Mobile Phase: ACN (A): 0.1% TFA in water (B) Flow rate: 1.5 mL/Min (S)—N-(1-cyanocyclopropyl)-5-cyclopropyl-4,4-difluoro-2-((S)-2,2,2-trifluoro-1-(4-(trifluoromethyl)phenyl)ethylamino)pentanamide

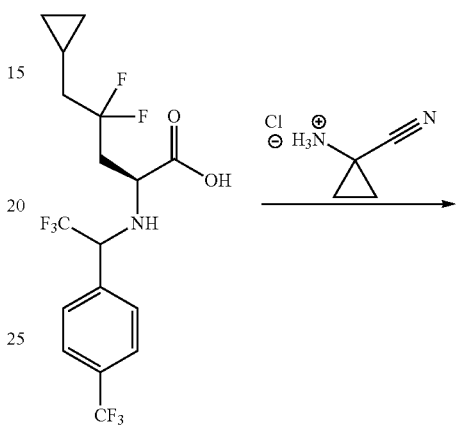

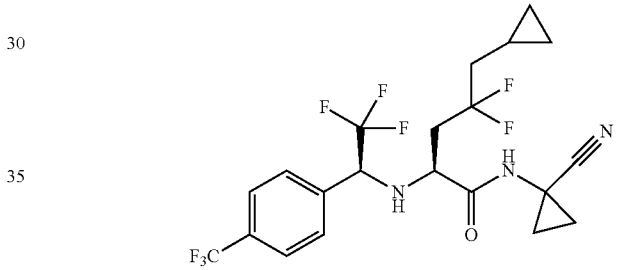

$^1$H-NMR (500 MHz, CD$_3$OD): 7.76, 7.62 (4H, A$_2$B$_2$, Ar—H), 4.38 (1H, m, CHCF$_3$), 3.52 (1H, m, CH), 2.38 (2H, m, CH$_2$), 1.83 (2H, m, CH$_2$), 1.40 (2H, m, CH$_2$), 1.02 (1H, m, CH), 0.82 (2H, m, CH$_2$), 0.53 (2H, m, CH$_2$), 0.19 (2H, m, CH$_2$). $^{19}$F-NMR (500 MHz, CD$_3$OD): EIMS (m/z): 484 (M+HPLC: 93.13% (RT 17.14) Column used zorbax SB, C8, 250×4.6 mm, 5 u Mobile Phase: ACN (A): 0.1% TFA in water (B) Flow rate: 1.5 mL/Min

BIOLOGICAL EXAMPLES

Biological Example 1

Cathepsin B Assay

Solutions of test compounds in varying concentrations were prepared in 10 μL of dimethyl sulfoxide (DMSO) and then diluted into assay buffer (40 μL, comprising: N,N-bis(2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 μL of assay buffer) was added to the dilutions. The assay solutions were mixed for 5-10 seconds on a shaker plate, covered and incubated for 30 min at room temperature. Z-FR-AMC (20 nMoles in 25 μL of assay buffer) was added to the assay solutions and hydrolysis was followed spectrophotometrically at (λ460 nm) for 5 min. Apparent inhibition

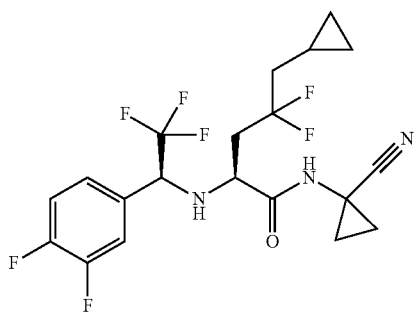

constants ($K_i$) were calculated from the enzyme progress curves using standard mathematical models.

Compounds of the invention were tested by the above-described assay and observed to exhibit cathepsin B inhibitory activity.

Biological Example 2

Cathepsin K Assay

Solutions of test compounds in varying concentrations were prepared in 10 µL of dimethyl sulfoxide (DMSO) and then diluted into assay buffer (40 µL, comprising: MES, 50 mM (pH 5.5); EDTA, 2.5 mM; and DTT, 2.5 mM). Human cathepsin K (0.0906 pMoles in 25 µL of assay buffer) was added to the dilutions. The assay solutions were mixed for 5-10 seconds on a shaker plate, covered and incubated for 30 min at room temperature. Z-Phe-Arg-AMC (4 nMoles in 25 µL of assay buffer) was added to the assay solutions and hydrolysis was followed spectrophotometrically at ($\lambda$460 nm) for 5 min. Apparent inhibition constants ($K_i$) were calculated from the enzyme progress curves using standard mathematical models.

Compounds of the invention were tested by the above-described assay and observed to exhibit cathepsin K inhibitory activity.

Biological Example 3

Cathepsin L Assay

Solutions of test compounds in varying concentrations were prepared in 10 µL of dimethyl sulfoxide (DMSO) and then diluted into assay buffer (40 mL, comprising: MES, 50 mM (pH 5.5); EDTA, 2.5 mM; and DTT, 2.5 mM). Human cathepsin L (0.05 pMoles in 25 µL of assay buffer) was added to the dilutions. The assay solutions were mixed for 5-10 seconds on a shaker plate, covered and incubated for 30 min at room temperature. Z-Phe-Arg-AMC (1 nMoles in 25 µL of assay buffer) was added to the assay solutions and hydrolysis was followed spectrophotometrically at ($\lambda$460 nm) for 5 min. Apparent inhibition constants ($K_i$) were calculated from the enzyme progress curves using standard mathematical models.

Compounds of the invention were tested by the above-described assay and observed to exhibit cathepsin L inhibitory activity.

Biological Example 4

Cathepsin S Assay

Solutions of test compounds in varying concentrations were prepared in 10 µL of dimethyl sulfoxide (DMSO) and then diluted into assay buffer (40 µL, comprising: MES, 50 mM (pH 6.5); EDTA, 2.5 mM; and NaCl, 100 mM); β-mercaptoethanol, 2.5 mM; and BSA, 0.00%. Human cathepsin S (0.05 pMoles in 25 µL of assay buffer) was added to the dilutions. The assay solutions were mixed for 5-10 seconds on a shaker plate, covered and incubated for 30 min at room temperature. Z-Val-Val-Arg-AMC (4 nMoles in 25 µL, of assay buffer containing 10% DMSO) was added to the assay solutions and hydrolysis was followed spectrophotometrically (at $\lambda$ 460 nm) for 5 min. Apparent inhibition constants ($K_i$) were calculated from the enzyme progress curves using standard mathematical models.

Compounds of the invention were tested by the above-described assay and observed to exhibit cathepsin S inhibitory activity.

Biological Example 5

Cathepsin F Assay

Solutions of test compounds in varying concentrations were prepared in 10 µL of dimethyl sulfoxide (DMSO) and then diluted into assay buffer (40 µL, comprising: MES, 50 mM (pH 6.5); EDTA, 2.5 mM; and NaCl, 100 mM); DTT, 2.5 mM; and BSA, 0.01%. Human cathepsin F (0.1 pMoles in 25 µl, of assay buffer) was added to the dilutions. The assay solutions were mixed for 5-10 seconds on a shaker plate, covered and incubated for 30 min at room temperature. Z-Phe-Arg-AMC (2 nMoles in 25 µL of assay buffer containing 10% DMSO) was added to the assay solutions and hydrolysis was followed spectrophotometrically (at $\lambda$460 nm) for 5 min. Apparent inhibition constants ($K_i$) were calculated from the enzyme progress curves using standard mathematical models.

Compounds of the invention were tested by the above-described assay and observed to exhibit cathepsin F inhibitory activity. Representative data for the assays above is provided in the Table below.

| Compound | Table of Cathepsin Activity | | | | |
|---|---|---|---|---|---|
| | Cathepsin S ($K_i$) | Cathepsin F ($K_i$) | Cat K-HURAB ($K_i$) | Cathepsin L ($K_i$) | Cathepsin B ($K_i$) |
| [structure] | (++++) | (++) | (++) | (+++) | (+++) |

-continued

Table of Cathepsin Activity

| Compound | Cathepsin S (K$_i$) | Cathepsin F (K$_i$) | Cat K-HURAB (K$_i$) | Cathepsin L (K$_i$) | Cathepsin B (K$_i$) |
| --- | --- | --- | --- | --- | --- |
| (structure) | (++++) | (+) | (++) | (++) | (+) |
| (structure) | (++++) | (+++) | (+++) | (+++) | (+++) |
| (structure) | (++++) | (+++) | (+++) | (+++) | (+++) |
| (structure) | (++++) | (+++) | (++++) | (+++) | (+++) |

| Compound | Cathepsin S ($K_i$) | Cathepsin F ($K_i$) | Cat K-HURAB ($K_i$) | Cathepsin L ($K_i$) | Cathepsin B ($K_i$) |
| --- | --- | --- | --- | --- | --- |
| [structure] | (++++) | (+++) | (+++) | (+++) | (+++) |
| [structure] | (++++) | | | | |
| [structure] | (++++) | | | | |

Activity legend: $K_i$ < 20 nM(++++); $K_i$ 21-500 nM(+++); $K_i$ 500 nM-5 uM(++); $K_i$ > 5 uM (+)

PHARMACEUTICAL FORMULATION EXAMPLES

Representative pharmaceutical formulations Containing a Compound of Formula (I)

Formulation Example 1

Oral Formulation

| | |
| --- | --- |
| Compound of Formula (I) | 10-100 mg |
| Citric Acid Monohydrate | 105 mg |
| Sodium Hydroxide | 18 mg |
| Flavoring | |
| Water | q.s. to 100 mL |

Formulation Example 2

Intravenous Formulation

| | |
| --- | --- |
| Compound of Formula (I) | 0.1-10 mg |
| Dextrose Monohydrate | q.s. to make isotonic |

| | |
|---|---|
| Citric Acid Monohydrate | 1.05 mg |
| Sodium Hydroxide | 0.18 mg |
| Water for Injection | q.s. to 1.0 mL |

Formulation Example 3

Tablet Formulation

| | |
|---|---|
| Compound of Formula (I) | 1% |
| Microcrystalline Cellulose | 73% |
| Stearic Acid | 25% |
| Colloidal Silica | 1% |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A compound having the following structure:

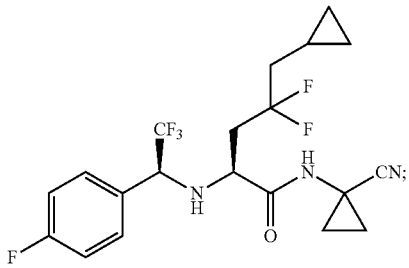 [SMILES: N#CC1(NC(=O)[C@H](CC(F)(F)CC2CC2)N[C@@H](c2ccc(F)cc2)C(F)(F)F)CC1]

or a pharmaceutically acceptable salt thereof.

* * * * *